(12) United States Patent
Luecking et al.

(10) Patent No.: US 7,456,191 B2
(45) Date of Patent: Nov. 25, 2008

(54) N-ARYL-SULFOXIMINE-SUBSTITUTED PYRIMIDINES AS CDK-AND/OR VEGF INHIBITORS, THEIR PRODUCTION AND USE AS PHARMACEUTICAL AGENTS

(75) Inventors: Ulrich Luecking, Berlin (DE); Gerhard Siemeister, Berlin (DE); Rolf Jautelat, Berlin (DE)

(73) Assignee: Schering AG, Berlin-Mitte (DE)

( * ) Notice: Subject to any disclaimer, the term of this patent is extended or adjusted under 35 U.S.C. 154(b) by 277 days.

(21) Appl. No.: 11/386,111

(22) Filed: Mar. 22, 2006

(65) Prior Publication Data

US 2006/0229325 A1 Oct. 12, 2006

Related U.S. Application Data

(60) Provisional application No. 60/665,862, filed on Mar. 29, 2005.

(30) Foreign Application Priority Data

Mar. 23, 2005 (EP) .................. 05090073

(51) Int. Cl.
*A01N 43/54* (2006.01)
*A61K 31/505* (2006.01)
*C07D 239/02* (2006.01)

(52) U.S. Cl. ...................... 514/275; 544/301
(58) Field of Classification Search .............. 514/275; 544/300
See application file for complete search history.

(56) References Cited

U.S. PATENT DOCUMENTS

2004/0224966 A1* 11/2004 Brumby et al. ............ 514/269

FOREIGN PATENT DOCUMENTS

WO   WO 02/096888   12/2002

OTHER PUBLICATIONS

Coburn M D et al., "Oxidation of 3,6-diamino-1,2,4,5-tetrazine and 3,6-diamino-1,2,4,5-tetrazine and 3,6-bis(S, S-dimethylsulfilimino)-1,2,4,5-tetrazine," Journal of Heterocyclic Chemistry, Dec. 1993, vol. 30, No. 6, pp. 1593-1595, XP002340372.

Claus P K et al., "N-Aryl sulfinimides" Tetrahedron, vol. 31, No. 6, 1975, pp. 505-510, XP002340373.

Pollak A et al., "Über Ringöffnungen einiger Azolo- und Azinoazine," Monatshefte Für Chemie, vol. 103, No. 5, 1972, pp. 1591-1603, XP002340374.

* cited by examiner

*Primary Examiner*—James Wilson
*Assistant Examiner*—Erich A Leeser
(74) *Attorney, Agent, or Firm*—Millen, White, Zelano & Branigan, P.C.

(57) ABSTRACT

This invention relates to pyrimidine derivatives of general formula (I)

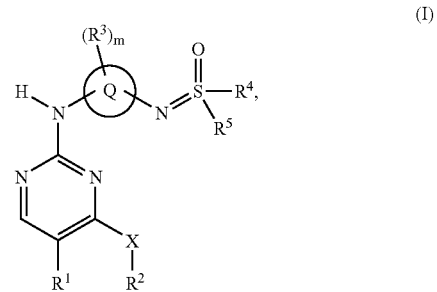

in which Q, R1, R2, R3, R4, R5, X, and m have the meanings that are contained in the description, as inhibitors of cyclin-dependent kinases and VEGF-receptor tyrosine kinases, their production as well as their use as medications for treatment of various diseases.

27 Claims, 1 Drawing Sheet

N-ARYL-SULFOXIMINE-SUBSTITUTED PYRIMIDINES AS CDK-AND/OR VEGF INHIBITORS, THEIR PRODUCTION AND USE AS PHARMACEUTICAL AGENTS

This application claims the benefit of the filing date of U.S. Provisional Application Ser. No. 60/665,862 filed Mar. 29, 2005 which is incorporated by reference herein.

This invention relates to N-Aryl-sulfoximine-substituted pyrimidine derivatives, their process for production as well as their use as pharmaceutical agents for treating various diseases.

The cyclin-dependent kinases (cyclin-dependent kinase, CDK) are an enzyme family that plays an important role in the regulation of the cell cycle and thus represents an especially advantageous target for the development of small inhibitory molecules. Selective inhibitors of the CDKs can be used for the treatment of cancer or other diseases that are caused by disorders of cell proliferation.

Receptor tyrosine kinases and their ligands, which specifically regulate the function of endothelial cells, are involved decisively in physiological as well as pathogenic angiogenesis. The Vascular Endothelial Growth Factor (VEGF)/VEGF-receptor system is of special importance here. In pathological situations, which are accompanied by increased neovascularization, such as, e.g., tumor diseases, an increased expression of angiogenic growth factors and their receptors was found. Inhibitors of the VEGF/VEGF receptor system can inhibit the build-up of a blood vessel system in the tumor, thus separate the tumor from the oxygen and nutrient supply and thus inhibit tumor growth.

Pyrimidines and analogs are already described as active ingredients, such as, for example, the 2-anilino-pyrimidines as fungicides (DE 4029650) or substituted pyrimidine derivatives for treatment of neurological or neurodegenerative diseases (WO 99/19305). As CDK inhibitors, the most varied pyrimidine derivatives are described, for example, bis(anilino)-pyrimidine derivatives (WO 00/12486), 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

In particular, pyrimidine derivatives that exhibit inhibitory actions relative to CDKs were disclosed in WO 02/096888 and WO 03/7076437. Compounds that contain a phenylsulfonamide group are known as inhibitors of the human carboanhydrases (especially carboanhydrase-2) and are used as diuretics, i.a., for treating glaucoma. The nitrogen atom and the oxygen atoms of the sulfonamide bind via hydrogen bridges to the zinc$^{2+}$ ion and the amino acid Thr 199 in the active center of carboanhydrase-2 and thus block their enzymatic function (A. Casini, F. Abbate, A. Scozzafava, C. T. Supuran, *Bioorganic. Med. Chem L.* 2003, 1, 2759.3). The clinical use of CDK inhibitors, which contain a phenylsulfonamide group, could be limited by the possibility of the inhibition of carboanhydrases and a side-effect spectrum that results therefrom.

Sulfoximines, such as, for example, sulfonimidoyl-modified triazoles as fungicides (H. Kawanishi, H. Morimoto, T. Nakano, T. Watanabe, K. Oda, K. Tsujihara, *Heterocycles* 1998, 49, 181) or arylalkylsulfoximines as herbicides and pesticides (Shell International Research, Ger. P. 2 129 678) are described as active ingredients.

The object of this invention is to provide compounds that exhibit better pharmaceutical properties, especially a reduction of carboanhydrase-2 inhibition, than the already known CDK inhibitors.

It was now found that compounds of general formula (I)

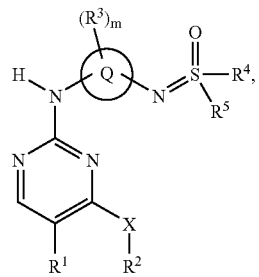

in which

Q stands for phenyl or a monocyclic Heteroaryl $R^1$ stands for halogen, —$CF_3$, $C_1$-$C_4$-Alkyl or Nitro, $R^2$ stands for $C_1$-$C_{10}$-alkyl, $C_2$-$C_{10}$-alkenyl, $C_2$-$C_{10}$-alkinyl, $C_3$-$C_{10}$-cycloalkyl, heterocyclyl with 3 to 7 ring atoms, $C_n$-aryl or heteroaryl with 5 to 10 ring atoms, each of which can optionally be substituted in one or more places, in the same way or differently, with (i) hydroxy, halogen, —$NR^7R^8$ or with the group —$C(O)R^6$, and/or (ii) $C_1$-$C_4$-alkyl, $C_2$-$C_4$-alkenyl, $C_1$-$C_4$-alkoxy, $C_2$-$C_4$-alkinyl, which can optionally be substituted in one or more places, in the same way or differently, with hydroxy, halogen, —$NR^7R^8$ or with the group —$C(O)R^6$ X stands for —O—, —S— or for the group —NH— or —$NR^{11}$—, wherein $R^{11}$ is a $C_1$-$C_3$-Alkyl or in case X stands for the group —$NR^{11}$—

$R^2$, $R^{11}$ and X form together a heterocyclyl ring with 3 to 7 ring atoms, which optionally can contain one or more additional heteroatoms and optionally can be substituted in one or more places, in the same way or differently with hydroxy, $C_1$-$C_3$-alkyl, $C_1$-$C_3$-alkoxy, —$NR^7R^8$ or halogen, $R^3$ stands for hydroxy, halogen, —$CF_3$, —$OCF_3$ or for the group —$NR^7R^8$, or for $C_1$-$C_6$-alkyl, $C_3$-$C_6$-cycloalkyl or $C_1$-$C_6$-alkoxy, each of which can optionally be substituted in one or more places, in the same way or differently with halogen, hydroxy or the group —$NR^7R^8$, m stands for 0-4, $R^4$ and $R^5$ in each case independently of one another, stand for $C_1$-$C_6$-alkyl, $C_1$-$C_6$-alkenyl or $C_3$-$C_6$-cycloalkyl, each of which can optionally be substituted in one or more places, in the same way or differently, with hydroxy, halogen, $C_1$-$C_3$-alkoxy, $C_1$-$C_3$-alkylthio, cyano, $C_3$-$C_6$-cycloalkyl, $C_1$-$C_6$-hydroxyalkyl, $C_2$-$C_6$-alkenyl, $C_2$-$C_6$-alkinyl or with the group —$CF_3$, —$OCF_3$ or —$NR^7R^8$, or $R^4$ and $R^5$ together form a ring of the group

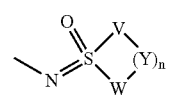

whereby
V, W and Y stand for —$CH_2$—, which are optionally and independently substituted in one or more places, in the same way or differently, with halogen, hydroxy, $C_1$-$C_6$-alkyl, $C_1$-$C_6$-alkoxy or —$NR^7R^8$, n stands for 0-4, $R^6$ stands for hydrogen or $C_1$-$C_6$-alkyl, $C_1$-$C_6$-alkoxy or $C_3$-$C_6$-cycloalkyl, each of which may optionally be substituted in one or more places, in the same way or differently, with $C_1$-$C_6$-alkyl, $R^7$ and $R^8$ in each case independently of one another, stand for hydrogen, $C_1$-$C_6$-alkyl, $C_1$-$C_6$-alkoxy, hydroxy-$C_1$-$C_6$-alkyl, dihydroxy-$C_1$-$C_6$-alkyl, phenyl, heteroaryl or for the group —$(CH_2)_p NR^9R^{10}$ or $R^7$ and $R^8$ form together with the nitrogen atom a heterocycyl ring with 3 to 7 ring atoms which optionally can contain one or more nitrogen, oxygen and/or sulfur atoms and/or can be interrupted by one or more —C(O)— groups in the ring, $R^9$ and $R^{10}$ in each case independently of one another, stand for hydrogen, $C_1$-$C_6$-alkyl, hydroxy-$C_1$-$C_6$-alkyl, dihydroxy-$C_1$-$C_6$-alkyl and p stands for 0-4, as well as their diastereomers, enantiomers and/or salts, inhibit cyclin-dependent kinases and VEGF receptor tyrosine kinases already in the nanomolar range and thus can inhibit the proliferation of tumor cells and/or tumor angiogenesis, whereby they simultaneously are no longer able to inhibit carboanhydrases and therefore reduce possible side effects.

The present application is based on the following definitions:

$C_n$-alkyl $C_n$-alkyl is defined in each case as a monovalent, straight-chain or branched saturated carbon hydrogen group with n carbon atoms.

A $C_1$-$C_6$ alkyl group encompasses for example:

methyl-, ethyl-, propyl-, butyl-, pentyl-,hexyl-, iso-propyl-, iso-butyl-, sec-butyl, tert-butyl-, iso-pentyl-, 2-methylbutyl-, 1-methylbutyl-, 1-ethylpropyl-, 1,2-dimethylpropyl, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-.

Preferred is a methyl, ethyl or propyl group.

$C_n$-alkenyl monovalent, straight-chain or branched carbon hydrogen group with n carbon atoms with at least one double bond.

A $C_2$-$C_6$-alkenyl group encompasses for example:

vinyl-, allyl-, (E)-2-methylvinyl-, (Z)-2-methylvinyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, Isopropenyl-, 2-methylprop-2-enyl-, 1-methylprop-2-enyl-, 2-methylprop-1-enyl-, (E)-1-methylprop-1-enyl-, (Z)-1-methylprop-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-Isopropylprop-2-enyl-, 1-Isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-Isopropylprop-1-enyl-, (E)-1-isopropylprop-1-enyl-, (Z)-1-Isopropylprop-1-enyl-, (E)-3,3-dimethylprop-1-enyl-, (Z)-3,3-dimethylprop-1-enyl-, 1-(1,1-dimethylethyl) ethenyl.

Preferred is a vinyl or allyl group.

$C_n$-alkinyl monovalent, straight-chain or branched carbon hydrogen group with n carbon atoms with at least one triple bond.

A $C_2$-$C_6$ alkinyl group encompasses for example:

ethinyl-, prop-1-inyl-, prop-2-inyl-, but-1-inyl-, but-2-inyl-, but-3-inyl-, pent-1-inyl-, pent-2-inyl-, pent-3-inyl-, pent-4-inyl-, hex-1-inyl-, hex-2-inyl-, hex-3-inyl-, hex-4-inyl-, hex-5-inyl-, 1-methylprop-2-inyl-, 2-methylbut-3-inyl-, 1-methylbut-3-inyl-, 1-methylbut-2-inyl-, 3-methylbut-1-inyl-, 1-Ethylprop-2-inyl-, 3-methylpent-4-inyl, 2-methylpent-4-inyl, 1-methyl-pent-4-inyl, 2-methylpent-3-inyl, 1-methylpent-3-inyl, 4-methylpent-2-inyl, 1-methylpent-2-inyl, 4-methylpent-1-inyl, 3-methylpent-1-inyl, 2-ethylbut-3-inyl-, 1-ethyl-but-3-inyl-, 1-ethylbut-2-inyl-, 1-propylprop-2-inyl-, 1-Isopropylprop-2-inyl-, 2,2-dimethyl-but-3-inyl-, 1,1-dimethylbut-3-inyl-, 1,1-dimethylbut-2-inyl- or 3,3-dimethyl-but-1-inyl-group.

Preferred is an ethinyl-, prop-1-inyl-oder prop-2-inyl-group.

$C_n$-cycloalkyl monovalent, saturated carbon hydrogen ring with n carbon atoms.

A $C_3$-$C_9$-cyclolalkyl ring encompasses for example:

cyclopropyl-, cyclobutyl-, cyclopentyl-, cyclohexyl-cycloheptyl-, cyclooctyl- or a cyclononyl-ring.

Preferred is a cyclopropyl, cylopentyl and a cyclohexyl ring.

$C_n$-alkoxy straight-chain or branched $C_n$-alkyl ether of the formula —OR with R=alkyl.

$C_n$-aryl $C_n$-aryl is a monovalent, aromatic ring system without a heteroatom with n carbon atoms.

$C_{10}$-aryl is naphtyl.

$C_6$-aryl is phenyl.

Preferred is phenyl.

Heteroatom

A heteroatom is an oxygen, sulfur or nitrogen atom.

Heteroaryl heteroaryl is a monovalent, aromatic ring system with at least one heteroatom. The binding valence is at a carbon atom or at a nitrogen atom.

A monocyclic heteroaryl according to the invention has one ring system and 5 or 6 ring atoms.

Heteroaryl rings with 5 ring atoms encompasses for example:

thienyl, thiazolyl, furanyl, pyrrolyl, oxazolyl, imidazolyl, pyrazolyl, isoxazolyl, isothiazolyl, oxadiazolyl, triazolyl, tetrazolyl and thiadiazolyl.

Heteroaryl rings with 6 ring atoms encompasses for example:

pyridyl, pyridazinyl, pyrimidinyl, pyrazinyl and triazinyl.

A bicyclic heteroaryl according to the invention has 9 or 10 ring atoms and two ring systems which have two adjacent ring atoms in common.

Heteroaryl rings with 9 ring atoms encompasses for example:

phthalidyl-, thiophthalidyl-, indolyl-, isoindolyl-, indazolyl-, benzothiazolyl-, indolonyl-, isoindolonyl-, benzofuranyl, benzothienyl, benzimidazolyl, benzoxazolyl, azocinyl, indolizinyl, purinyl.

Heteroaryl rings with 10 ring atoms encompasses for example:

Isoquinolinyl-, quinolinyl-, benzoxazinonyl-, phthalazinonyl, quinolonyl-, isoquinolonyl-, quinazolinyl-, quinoxalinyl-, cinnolinyl-, phthalazinyl-, 1,7- or 1,8-naphthyridinyl-, quinolinyl-, isoquinolinyl-, quinazolinyl- or a quinoxalinyl-ring.

Monocyclic heteroaryl rings with 5 or 6 ring atoms are preferred.

Heterocyclyl heterocyclyl as defined herein is a completely hydrogenated heteroaryl (completely hydrogenated heteroaryl=saturated heterocyclyl) i.e. a non-aromatic ring system with at least one heteroatom. The binding valence is at an carbon atom or at a nitrogen atom.

A heterocyyl ring with 3 ring atoms is for example aziridinyl.

A heterocyyl ring with 4 ring atoms is for example azetidinyl.

Heterocyyl rings with 5 ring atoms encompasses for example the rings:

pyrrolidinyl, imidazolidinyl and pyrazolidinyl.

Heterocyyl rings with 6 ring atoms encompasses for example the rings:

piperidinyl, piperazinyl, morpholinyl and thiomorphinyl.

Heterocyyl rings with 7 ring atoms encompasses for example the rings:

azepanyl, [1,3]-diazepanly and [1,4]-diazepanyl.

Halogen halogen encompasses fluorine, chlorine, bromine and iodine.

Preferred is bromine.

In principle, stereoisomers have the same structure (constitution)—and thus also the same summation formula—but are distinguished by the spatial arrangement of the atoms.

In general, configurational isomers and conformational isomers are distinguished. Configurational isomers are stereoisomers that can be converted into one another only by bond breaking. These include enantiomers, diastereomers and E/Z (cis/trans) isomers.

Enantiomers are stereoisomers that behave toward one another like image and mirror image and do not have any symmetry plane. All stereoisomers that are not enantiomers are referred to as diastereomers. E/Z (cis/trans) isomers of double bonds are a special case.

Conformational isomers are stereoisomers that can be converted into one another by the turning of single bonds.

To differentiate the types of isomerism from one another, see also the IUPAC rules, Section E (Pure Appl. Chem. 45, 11-30, 1976).

If an acid group is included, the physiologically compatible salts of organic and inorganic bases, such as, for example, the readily soluble alkali salts and earth-alkaline salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol, are suitable as salts.

If a basic group is included, the physiologically compatible salts of organic and inorganic acids, such as hydrochloric acid, sulfuric acid, phosphoric acid, citric acid, or tartaric acid, i.a., are suitable.

In the general formula (I) Q can stand for:
phenyl or a monocyclic heteroaryl.
Preferably Q stands for phenyl.
In the general formula (I) $R^1$ can stand for:
halogen, —$CF_3$, $C_1$-$C_4$-Alkyl or Nitro.
Preferably $R^1$ stands for halogen, —$CF_3$, $C_1$-$C_2$-Alkyl or Nitro.
Most preferably $R^1$ stands for bromine.
In the general formula (I) $R^2$ can stand for:
$C_1$-$C_{10}$-alkyl, $C_2$-$C_{10}$-alkenyl, $C_2$-$C_{10}$-alkinyl, $C_3$-$C_{10}$-cycloalkyl, heterocyclyl with 3 to 7 ring atoms, $C_n$-aryl or a mono- or bicyclic heteroaryl ring, each of which can optionally be substituted in one or more places, in the same way or differently, with (i) hydroxy, halogen, —$NR^7R^8$ or with the group —$COR^6$, and/or (ii) $C_1$-$C_4$-alkyl, $C_2$-$C_4$-alkenyl, $C_1$-$C_4$-alkoxy, $C_2$-$C_4$-alkinyl, which can optionally be substituted in one or more places, in the same way or differently, with hydroxy, halogen, —$NR^7R^8$ or with the group —$COR^6$.

Preferably $R^2$ stands for:

$C_1$-$C_{10}$-alkyl, $C_2$-$C_{10}$-alkinyl, $C_3$-$C_{10}$-cycloalkyl, heterocyclyl with 3 to 7 ring atoms, $C_n$-aryl or a monocyclic heteroaryl each of which can optionally be substituted in one or more places, in the same way or differently, with hydroxy and/or $C_1$-$C_4$-alkyl, which can optionally be substituted in one or more places, in the same way or differently with hydroxyl.

More preferably $R^2$ stands for:

$C_2$-$C_6$-alkyl, $C_2$-$C_8$-alkinyl, $C_4$-$C_7$-cycloalkyl, heterocyclyl with 5 to 7 ring atoms, phenyl or a monocyclic heteroaryl with 6 ring atoms each of which can optionally be substituted in one or more places, in the same way or differently, with hydroxy and/or $C_1$-$C_4$-alkyl, which can optionally be substituted in one or more places, in the same way or differently with hydroxyl.

Even more preferably $R^2$ stands for:

$C_3$-$C_5$-alkyl, $C_3$-$C_5$-alkinyl, $C_5$-$C_6$-cycloalkyl, heterocyclyl with 6 ring atoms, phenyl or monocyclic heteroaryl with 6 ring atoms and only one heteroatom each of which can optionally be substituted in one or more places, in the same way or differently, with hydroxy and/or $C_1$-$C_4$-alkyl, which can optionally be substituted in one or more places, in the same way or differently with hydroxyl.

In the general formula (I) X can stand for:
—O—, —S— or for the group —NH— or —NR$^{11}$—, wherein R$^{11}$ is a C$_1$-C$_3$-Alkyl or
in case X stands for the group —NR$^{11}$—:
R$^2$, R$^{11}$ and X form together a heterocyclyl ring with 3 to 7 ring atoms, which optionally can contain one or more additional heteroatoms and optionally can be substituted in one or more places, in the same way or differently, with hydroxy, C$_1$-C$_3$-alkyl, C$_1$-C$_3$-alkoxy, —NR$^7$R$^8$ or halogen.

Preferably X stands for:
—O—, —S— or for the group —NH—
More preferably X stands for —NH—.

In the general formula (I) R$^3$ can stand for:
hydroxy, halogen, —CF$_3$, —OCF$_3$ or for the group —NR$^7$R$^8$, or for C$_1$-C$_6$-alkyl, C$_3$-C$_6$-cycloalkyl or C$_1$-C$_6$-alkoxy, each of which can optionally be substituted in one or more places, in the same way or differently with halogen, hydroxy or the group —NR$^7$R$^8$.

In the general formula (I) m can stand for:
0-4, preferably for 0 or 1, even more preferred for 0.

In the general formula (I) R$^4$ and R$^5$ can stand for:
in each case independently of one another C$_1$-C$_6$-alkyl, C$_1$-C$_6$-alkenyl or C$_3$-C$_6$-cycloalkyl, each of which can optionally be substituted in one or more places, in the same way or differently, with hydroxy, halogen, C$_1$-C$_3$-alkoxy, C$_1$-C$_3$-alkylthio, cyano, C$_3$-C$_6$-cycloalkyl, C$_1$-C$_6$-hydroxyalkyl, C$_2$-C$_6$-alkenyl, C$_2$-C$_6$-alkinyl or with the group —CF$_3$, —OCF$_3$ or —NR$^7$R$^8$, or
R$^4$ and R$^5$ together form a ring of the group

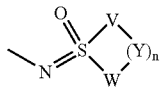

whereby
V, W and Y stand for —CH$_2$—, which are optionally and independently substituted in one or more places, in the same way or differently, with halogen, hydroxy, C$_1$-C$_6$-alkyl, C$_1$-C$_6$-alkoxy or —NR$^7$R$^8$,
n stands for 0-4.

More preferably R$^4$ and R$^5$ independently stand for:
C$_1$-C$_6$-alkyl which can optionally be substituted in one or more places, in the same way or differently, with hydroxy, halogen, C$_1$-C$_3$-alkoxy, C$_1$-C$_6$-hydroxyalkyl or —NR$^7$R$^8$ or
R$^4$ and R$^5$ together form a ring of the group

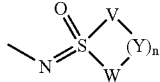

whereby
V, W and Y stand for —CH$_2$—, which are optionally and independently substituted in one or more places, in the same way or differently, with halogen, hydroxy, C$_1$-C$_6$-alkyl, C$_1$-C$_6$-alkoxy or —NR$^7$R$^8$,
n stands for 1-3.

Even more preferably R$^4$ and R$^5$ independently stand for C$_1$-C$_6$-alkyl which can optionally be substituted in one or more places, in the same way or differently, with hydroxyl or —NR$^7$R$^8$ or R$^4$ and R$^5$ together form a ring of the group

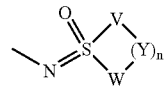

whereby
V, W and Y stand for —CH$_2$—, which are optionally and independently substituted in one or more places in the same way or differently with hydroxyl or —NR$^7$R$^8$
n stands for 1-3.

Most preferred R$^4$ and R$^5$ independently stand for C$_1$-C$_6$-alkyl or
R$^4$ and R$^5$ together form a ring of the group

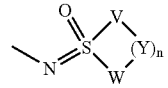

whereby
V, W and Y stand for —CH$_2$— and
n stands for 2.

In the general formula (I) R$^6$ can stand for:
hydrogen or C$_1$-C$_6$-alkyl, C$_1$-C$_6$-alkoxy or C$_3$-C$_6$-cycloalkyl, each of which may optionally be substituted in one or more places, in the same way or differently, with C$_1$-C$_6$-alkyl.

In the general formula (I) R$^7$ and R$^8$ can stand for:
in each case independently of one another hydrogen, C$_1$-C$_6$-alkyl, C$_1$-C$_6$-alkoxy, hydroxy-C$_1$-C$_6$-alkyl, dihydroxy-C$_1$-C$_6$-alkyl, phenyl, heteroaryl or for the group —(CH$_2$)$_p$NR$^9$R$^{10}$ or
R$^7$ and R$^8$ form together with the nitrogen atom a heterocycyl ring with 3 to 7 ring atoms which optionally
    (i) can contain one or more nitrogen, oxygen and/or sulfur atoms and/or
    (ii) can be interrupted by one or more —C(O)— groups in the ring and/or
    (iii) can be substituted by hydroxy, C$_1$-C$_6$-alkyl, C$_1$-C$_6$-alkoxy, hydroxy-C$_1$-C$_6$-alkyl or dihydroxy-C$_1$-C$_6$-alkyl.

More preferably R$^7$ and R$^8$ stand for:
in each case independently of one another hydrogen, C$_1$-C$_6$-alkyl, hydroxy-C$_1$-C$_6$-alkyl, dihydroxy-C$_1$-C$_6$-alkyl or for the group —(CH$_2$)$_p$NR$^9$R$^{10}$ or
R$^7$ and R$^8$ form together with the nitrogen atom a heterocycyl ring with 5 or 6 ring atoms which optionally can be interrupted by one —C(O)— group in the ring and/or can be substituted by hydroxy, C$_1$-C$_6$-alkyl, hydroxy-C$_1$-C$_6$-alkyl or dihydroxy-C$_1$-C$_6$-alkyl.

In the general formula (I) R$^9$ and R$^{10}$ can stand for:
in each case independently of one another hydrogen, C$_1$-C$_6$-alkyl, hydroxy-C$_1$-C$_6$-alkyl, dihydroxy-C$_1$-C$_6$-alkyl.

In the general formula (I) p can stand for 0-4, preferably 1-2.

Preferable compounds of general formula I are those wherein
Q stands for phenyl or a monocyclic heteroaryl,
R$^1$ stands for halogen, —CF$_3$, C$_1$-C$_4$-Alkyl or Nitro,
R$^2$ stands for C$_1$-C$_{10}$-alkyl, C$_2$-C$_{10}$-alkinyl, C$_3$-C$_{10}$-cycloalkyl, heterocyclyl with 3 to 7 ring atoms, C$_n$-aryl or a monocyclic heteroaryl each of which can optionally be substituted in one or more places, in the same way or differently, with hydroxy and/or $C_1$-$C_4$-alkyl, which can optionally be substituted in one or more places, in the same way or differently with hydroxyl, X stands for —O—, —S— or for the group —NH—

$R^3$ stands for hydroxy, halogen, —$CF_3$, —$OCF_3$ or for the group —$NR^7R^8$, or for $C_1$-$C_6$-alkyl, $C_3$-$C_6$-cycloalkyl or $C_1$-$C_6$-alkoxy, each of which can optionally be substituted in one or more places, in the same way or differently with halogen, hydroxy or the group —$NR^7R^8$, m stands for 0 or 1, $R^4$ and $R^5$ independently stand for $C_1$-$C_6$-alkyl which can optionally be substituted in one or more places, in the same way or differently, with hydroxy, halogen, $C_1$-$C_3$-alkoxy, $C_1$-$C_6$-hydroxyalkyl or —$NR^7R^8$ or $R^4$ and $R^5$ together form a ring of the group

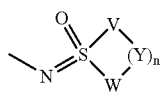

whereby

V, W and Y stand for —$CH_2$—, which are optionally and independently substituted in one or more places, in the same way or differently, with halogen, hydroxy, $C_1$-$C_6$-alkyl, $C_1$-$C_6$-alkoxy or —$NR^7R^8$, n stands for 1-3, $R^7$ and $R^8$ in each case independently of one another stand for hydrogen, $C_1$-$C_6$-alkyl, hydroxy-$C_1$-$C_6$-alkyl, dihydroxy-$C_1$-$C_6$-alkyl or for the group —$(CH_2)_pNR^9R^{10}$ or $R^7$ and $R^8$ form together with the nitrogen atom a heterocycyl ring with 5 or 6 ring atoms which optionally can be interrupted by one —C(O)— group in the ring and/or can be substituted by hydroxy, $C_1$-$C_6$-alkyl, hydroxy-$C_1$-$C_6$-alkyl or dihydroxy-$C_1$-$C_6$-alkyl, as well as their diastereomers, enantiomers and/or salts.

Other preferable compounds of general formula (I) are those wherein

Q stands for phenyl or 5 to 6 membered heteroaryl, $R^1$ stands for halogen or —$CF_3$, $R^2$ stands for $C_1$-$C_{10}$-alkyl optionally substituted in one or more places, with hydroxy, X stands for oxygen, sulfur or for the group —NH—

$R^3$ stands for hydroxy, halogen, —$CF_3$, —$OCF_3$ or for the group —$NR^7R^8$, or for $C_1$-$C_6$-alkyl, $C_3$-$C_6$-cycloalkyl or $C_1$-$C_6$-alkoxy, each of which can optionally be substituted in one or more places, in the same way or differently with halogen, hydroxy or the group —$NR^7R^8$, m stands for 0-4, $R^4$ and $R^5$ in each case independently of one another, stand for $C_1$-$C_6$-alkyl, $C_1$-$C_6$-alkenyl or $C_3$-$C_6$-cycloalkyl, each of which can optionally be substituted in one or more places, in the same way or differently, with hydroxy, halogen, $C_1$-$C_3$-alkoxy or with the group —$NR^7R^8$, or $R^4$ and $R^5$ together form a ring of the group

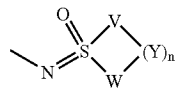

whereby

V, W and Y in each case independently of one another, stand for —$CH_2$— that is optionally substituted in one or more places, in the same way or differently, with halogen, hydroxy, $C_1$-$C_6$-alkyl, $C_1$-$C_6$-alkoxy or —$NR^7R^8$, n stands for 1-4 and $R^7$ and $R^8$ in each case independently of one another, stand for hydrogen, $C_1$-$C_6$-alkyl, $C_1$-$C_6$-alkoxy, hydroxy-$C_1$-$C_6$-alkyl, dihydroxy-$C_1$-$C_6$-alkyl, phenyl, heteroaryl as well as their isomers, diastereomers, enantiomers and/or salts.

More preferred compounds of general formula (I), are those wherein

Q stands for phenyl, $R^1$ stands for halogen, —$CF_3$, $C_1$-$C_2$-Alkyl or Nitro, $R^2$ stands for $C_1$-$C_{10}$-alkyl, $C_2$-$C_{10}$-alkinyl, $C_3$-$C_{10}$-cycloalkyl, heterocyclyl with 3 to 7 ring atoms, $C_n$-aryl or a monocyclic heteroaryl each of which can optionally be substituted in one or more places, in the same way or differently, with hydroxy and/or $C_1$-$C_4$-alkyl, which can optionally be substituted in one or more places, in the same way or differently with hydroxyl, X stands for —O—, —S— or for the group —NH— m stands for 0

$R^4$ and $R^5$ independently stand for $C_1$-$C_6$-alkyl or $R^4$ and $R^5$ together form a ring of the group

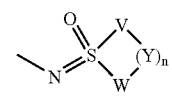

whereby

V, W and Y stand for —$CH_2$—, which are optionally and independently substituted in one or more places in the same way or differently with hydroxyl or —$NR^7R^8$ n stands for 1-3, as well as their diastereomers, enantiomers and/or salts.

Other more preferred compounds of general formula (I), are those wherein

Q stands for phenyl or 5 to 6 membered heteroaryl, $R^1$ stands for halogen or —$CF_3$, $R^2$ stands for $C_1$-$C_{10}$-alkyl optionally substituted in one or more places with hydroxy, X stands for oxygen, sulfur or for the group —NH—, m stands for 0, $R^4$ and $R^5$ in each case independently of one another, stand for $C_1$-$C_6$-alkyl or $C_3$-$C_6$-cycloalkyl, each of which can optionally be substituted in one or more places, in the same way or differently, with hydroxy, halogen, $C_1$-$C_3$-alkoxy or with the group —$NR^7R^8$ and $R^7$ and $R^8$ in each case independently of one another, stand for hydrogen, $C_1$-$C_6$-alkyl, $C_1$-$C_6$-alkoxy, hydroxy-$C_1$-$C_6$-alkyl, dihydroxy-$C_1$-$C_6$-alkyl or phenyl as well as their isomers, diastereomers, enantiomers and/or salts.

Even more preferred compounds of general formula (I), are those wherein
Q stands for phenyl,
$R^1$ stands for bromine,
$R^2$ stands for $C_3$-$C_5$-alkyl, $C_3$-$C_5$-alkinyl, $C_5$-$C_6$-cycloalkyl, heterocyclyl with 6 ring atoms, phenyl or monocyclic heteroaryl with 6 ring atoms and only one heteroatom each of which can optionally be substituted in one or more places, in the same way or differently, with hydroxy and/or $C_1$-$C_4$-alkyl, which can optionally be substituted in one or more places, in the same way or differently with hydroxyl,
X —NH—
m stands for 0
$R^4$ and $R^5$ independently stand for $C_1$-$C_6$-alkyl or
$R^4$ and $R^5$ together form a ring of the group

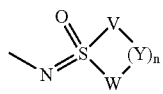

whereby
V, W and Y stand for —$CH_2$— and
n stands for 2, as well as their diastereomers, enantiomers and/or salts.

Other even more preferred compounds of general formula (I),
are those wherein
Q stands for phenyl,
$R^1$ stands for halogen,
$R^2$ stands for $C_1$-$C_{10}$-alkyl optionally substituted in one or more places with hydroxy,
X stands for oxygen or for the group —NH—,
m stands for 0 and
$R^4$ and $R^5$ in each case independently of one another, stand for $C_1$-$C_6$-alkyl as well as their isomers, diastereomers, enantiomers and/or salts.

Also object of the present invention are those compounds which result when possible, preferable or more preferable meanings of the substituents are combined.

Additionally preferred compounds are those which result when exemplified meanings of the substituents are combined.

The compounds according to the invention essentially inhibit cyclin-dependent kinases, upon which their action is based, for example, against cancer, such as solid tumors and leukemia; auto-immune diseases, such as psoriasis, alopecia and multiple sclerosis; chemotherapy agent-induced alopecia and mucositis; cardiovascular diseases, such as stenoses, arterioscieroses and restenoses; infectious diseases, such as, e.g., those caused by unicellular parasites, such as trypanosoma, toxoplasma or plasmodium, or those caused by fungi; nephrological diseases, such as, e.g., glomerulonephritis; chronic neurodegenerative diseases, such as Huntington's disease, amyotrophic lateral sclerosis, Parkinson's disease, AIDS, dementia and Alzheimer's disease; acute neurodegenerative diseases, such as ischemias of the brain and neurotraumas; and viral infections, such as, e.g., cytomegalic infections, herpes, hepatitis B and C, and HIV diseases.

The eukaryotic cell division cycle ensures the duplication of the genome and its distribution to the daughter cells by passing through a coordinated and regulated sequence of events. The cell cycle is divided into four successive phases: the G1 phase represents the time before the DNA replication, in which the cell grows and is sensitive to external stimuli. In the S phase, the cell replicates its DNA, and in the G2 phase, preparations are made for entry into mitosis. In mitosis (M phase), the replicated DNA separates, and cell division is complete.

The cyclin-dependent kinases (CDKs), a family of serine/threonine kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the above-mentioned cell cycle CDKs, while no specific function could be associated with other members of the CDK enzyme family. One of the latter, CDK5, is distinguished in that it has an atypical regulatory subunit (p35) that deviates from the cyclins, and its activity is highest in the brain.

Figure 1:
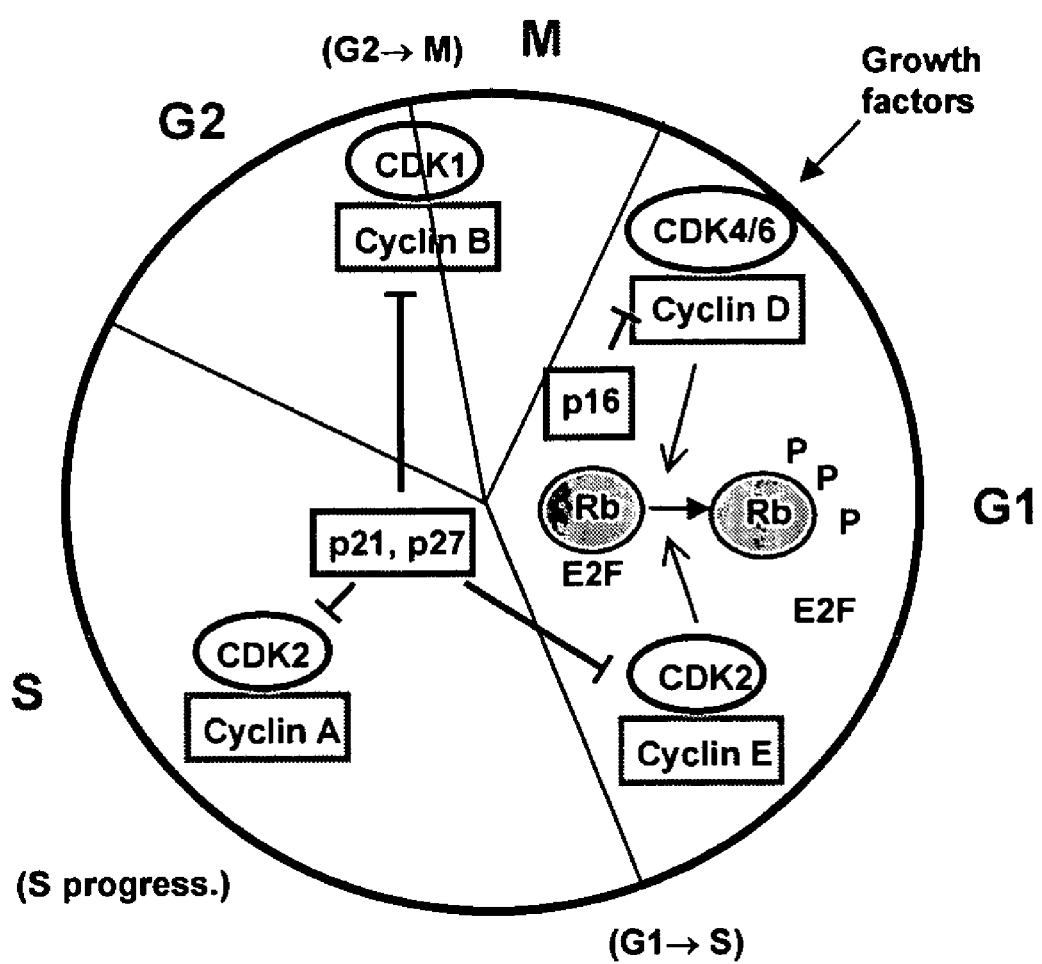
FIG. 1: Illustrates the cell cycle.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates transcription factors of the E2F type and forms transcriptional repressor complexes with histone-deacetylases (HDAC) (Zhang, H. S. et al. (2000). Exit from G1 and S Phase of the Cell Cycle is Regulated by Repressor Complexes Containing HDAC-Rb-hSWI/SNF and Rb-hSWI/SNF. Cell 101, 79-89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDKs is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory threonine and tyrosine radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1,2,4,6, but inhibit only the complexes that contain CDK1 or CDK2. Members of the p16 family are specific inhibitors of the CDK4- and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. *Science* 288, 1425-1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al., (1999). Selective Killing of Transformed Cells by Cyclin/Cyclin-Dependent Kinase 2 Antagonists. *Proc. Natl. Acad. Sci. USA* 96, 4325-4329).

Changes of the cell cycle control play a role not only in carcinoses. The cell cycle is activated by a number of viruses, both by transforming viruses as well as by non-transforming viruses, to make possible the reproduction of viruses in the host cell. The false entry into the cell cycle of normally post-mitotic cells is associated with various neurodegenerative diseases.

The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. *J. Med. Chem.* 43, 1-18; Fry, D. W. & Garrett, M. D. (2000). Inhibitors of Cyclin-Dependent Kinases as Therapeutic Agents for the Treatment of Cancer. *Curr. Opin. Oncol. Endo. Metab. Invest. Drugs* 2, 40-59; Rosiania, G. R. & Chang, Y. T. (2000). Targeting Hyperproliferative Disorders with Cyclin-Dependent Kinase Inhibitors. *Exp. Opin. Ther. Patents* 10, 215-230; Meijer, L. et al. (1999). Properties and Potential Applications of Chemical Inhibitors of Cyclin-Dependent Kinases. *Pharmacol. Ther.* 82, 279-284; Senderowicz, A. M. & Sausville, E. A. (2000). Preclinical and Clinical Development of Cyclin-Dependent Kinase Modulators. *J. Natl. Cancer Inst.* 92, 376-387).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure, or buffers. These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants such as salts of bile acids or animal or plant phospholipids, but also mixtures thereof as well as liposomes or their components, can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

In contrast, compounds of general formula I according to the invention can also inhibit receptor tyrosine kinases and their ligands that specifically regulate the function of endothelial cells. Receptor tyrosine kinases and their ligands that specifically regulate the function of endothelial cells are involved decisively in physiological as well as pathogenic angiogenesis. The VEGF/VEGF-receptor system is of special importance here. In pathological situations, which are accompanied by increased neovascularization, an increased expression of angiogenic growth factors and their receptors was found. Most solid tumors thus express large amounts of VEGF, and the expression of the VEGF receptors is preferably considerably increased in the endothelial cells that lie near the tumors or run through the latter (Plate et al., Cancer Res. 53, 5822-5827, 1993). The inactivation of the VEGF/VEGF receptor system by VEGF-neutralizing antibodies (Kim et al., Nature 362, 841-844, 1993), retroviral expression of dominant-negative VEGF-receptor variants (Millauer et al., Nature 367, 576-579, 1994), recombinant VEGF-neutralizing receptor variants (Goldman et al., Proc. Natl. Acad. Sci. USA 95, 8795-8800, 1998), or low-molecular inhibitors of the VEGF-receptor tyrosine kinase (Fong et al., Cancer Res. 59, 99-106, 1999; Wedge et al., Cancer Res. 60, 970-975, 2000; Wood et al., Cancer Res. 60, 2178-2189, 2000) resulted in a reduced tumor growth and a reduced tumor vascularization. Thus, the inhibition of the angiogenesis is a possible treatment method for tumor diseases.

Compounds according to the invention can consequently inhibit either cyclin-dependent kinases, such as CDK1, CDK2, CDK3, CDK4, CDK5, CDK6, CDK7, CDK8 and CDK9, as well as the glycogen-synthase-kinase (GSK-3β) and VEGF-receptor tyrosine kinases or cyclin-dependent kinases or VEGF-receptor tyrosine kinases. These actions contribute to the fact that the compounds according to the invention can be used in the treatment of cancer, angiofibroma, arthritis, eye diseases, auto-immune diseases, chemotherapy agent-induced alopecia and mucositis, Crohn's disease, endometriosis, fibrotic diseases, hemangioma, cardiovascular diseases, infectious diseases, nephrological diseases, chronic and acute neurodegenerative diseases, as well as injuries to the nerve tissue, viral infections, for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis, whereby cancer is defined as solid tumors, tumor or metastastic growth, Kaposi's sarcoma, Hodgkin's disease, and leukemia;

arthritis is defined as rheumatoid arthritis;

eye diseases are defined as diabetic retinopathy, and neovascular glaucoma;

auto-immune diseases are defined as psoriasis, alopecia and multiple sclerosis;

fibrotic diseases are defined as cirrhosis of the liver, mesangial cell proliferative diseases, and arteriosclerosis;

infectious diseases are defined as diseases that are caused by unicellular parasites;

cardiovascular diseases are defined as stenoses, such as, e.g., stent-induced restenoses, arterioscleroses and restenoses;

nephrological diseases are defined as glomerulonephritis, diabetic nephropathy, malignant nephrosclerosis, thrombic microangiopathic syndrome, transplant rejections and glomerulopathy;

chronic neurodegenerative diseases are defined as Huntington's disease, amyotrophic lateral sclerosis, Parkinson's disease, AIDS dementia and Alzheimer's disease;

acute neurodegenerative diseases are defined as ischemias of the brain and neurotraumas and viral infections are defined as cytomegalic infections, herpes, hepatitis B or C, and HIV diseases.

Subjects of this invention are also pharmaceutical agents for treating the above-cited diseases, which contain at least one compound according to general formula (I), as well as pharmaceutical agents with suitable diluents, carriers and/or vehicles.

The compounds of general formula I according to the invention are, i.a., excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β). Further to this compounds of the present invention inhibit VEGF-receptor tyrosine kinases.

Intermediate products preferably used for the production of the compounds of general formula I according to the invention are those of general formula (IIa),

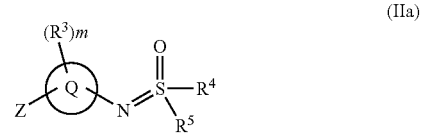

(IIa)

in which Z stands for —NH$_2$ or NO$_2$ and m, Q, R$^3$, R$^4$ and R$^5$ have the meanings which are indicated in any one of claims 1 to 19, as well as their diastereomers, enantiomers and salts and are also subjects of this invention.

Preferably Z stands for —NH$_2$.

Preferred intermediate products of general formula (IIa) are those of general formula (II)

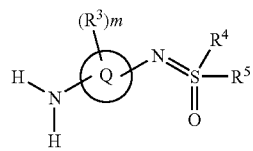

in which m, Q, R$^3$, R$^4$ and R$^5$ have the meanings which are indicated in any one of claims 1 to 19, as well as their diastereomers, enantiomers and salts and are also subjects of this invention.

Intermediate products preferably used for the production of the compounds of general formula (I) according to the invention are those of general formula (IIIa),

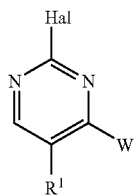

(IIIa)

in which

Hal stands for halogen, W stands for halogen, hydroxy, or X—R², and R¹, R², and X have the meanings which are indicated in any one of claims 1 to 19, as well as their diastereomers, enantiomers and salts and are also subjects of this invention. Preferred intermediate products of general formula (IIIa) are those of general formula (III),

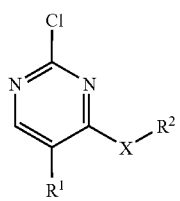

(III)

in which

X, R¹ and R² have the meanings which are indicated in any one of claims 1 to 19, as well as their diastereomers, enantiomers and salts and are also subjects of this invention.

If the production of the starting compounds is not described, the latter are known or can be produced in a way that is similar to known compounds or to processes that are described here. It is also possible to perform all reactions that are described here in parallel reactors or by means of combinatory operating procedures.

The isomer mixtures can be separated into enantiomers or E/Z isomers according to commonly used methods, such as, for example, crystallization, chromatography or salt formation.

The production of salts is carried out in the usual way by a solution of the compound of formula I being mixed with the equivalent amount of or an excess of a base or acid, which optionally is in solution, and the precipitate being separated or the solution being worked up in the usual way.

Production of the Compounds According to the Invention

One important method for the production of sulfoximines is the reaction of a sulfoxide with hydrazoic acid, which is produced in situ, e.g., from the reaction of sodium azide and concentrated sulfuric acid (M. Reggelin, C. Zur, *Synthesis* 2000, 1, 1). The reaction can be performed in an organic solvent, such as chloroform. Other methods for the synthesis of sulfoximines are, e.g., the reactions of sulfoxides with a) TsN₃ ((a) R. Tanaka, K. Yamabe, *J. Chem. Soc. Chem. Commun.* 1983, 329; (b) H. Kwart, A. A. Kahn, *J. Am. Chem. Soc.* 1967, 89, 1959))

b) N-Tosylimino Phenyl Iodinane and cat. Amounts of Cu(I)triflate (J. F. K. Müller, P. Vogt, *Tetrahedron Lett.* 1998, 39, 4805)

c) Boc-azide and cat. Amounts of Iron(II) Chloride (T. Bach, C. Korber, *Tetrahedron Lett.* 1998, 39, 5015)

d) o-Mesitylenesulfonylhydroxylamine (MSH) (C. R. Johnson, R. A. Kirchhoff, H. G. Corkins, *J. Org. Chem.* 1974, 39, 2458).

e) [N-(2-(Trimethylsilyl)ethanesulfonyl)imino]phenyliodinane (PhI=NSes) (S. Cren, T. C. Kinahan, C. L. Skinner and H. Tye, *Tetrahedron Lett.* 2002, 43, 2749).

f) Trifluoroacetamide, iodobenzene diacetate, magnesium oxide and [Rh₂(OAc)₄] (H. Okamura and C. Bolm, *Org. Lett.* 2004, 6, 1305).

The introduction of aromatic and heteroaromatic rings on to the nitrogen of sulfoximines can be achieved by palladium-, nickel- or copper-catalyzed cross-coupling reactions (a) C. Bolm, J. P. Hildebrandt, *Tetrahedron Lett.* 1998, 39, 5731-5734; b) M. Harmata, N. Parvi, Angew. Chemie 1999, 38, 2577-2579; c) C. Bolm, J. P. Hildebrandt, *J. Org. Chem.* 2000, 65, 169; d) C. Bolm, J. P. Hildebrand, J. Rudolph, *Synthesis* 2000, 911-913; e) C. Bolm, M. Verrucci, O. Simic, P. G. Cozzi, G. Raabe, H. Okamura, *Chem. Commun.* 2003, 22, 2826-2827; f) G. Y. Cho, P. Rémy, J. Jansson, C. Moessner, C. Bolm, *Org. Lett.* 2004, 6, 3293-3296.)

Another method for the production of N-Aryl-sulfoximines is the oxidation of N-arylsulfilimines (S.-L. Huang, D. Swern, *J. Org. Chem.* 1979, 44, 2510).

In terms of structure and configuration, sulfoximines generally have a high stability (C. Bolm, J. P. Hildebrand, *J. Org. Chem.* 2000, 65, 169). These properties of the functional group often also allow drastic reaction conditions and make possible the simple derivatization of the sulfoximines in the imine-nitrogen and α-carbon. Enantiomer-pure sulfoximines are also used as auxiliaries in the diastereoselective synthesis ((a) S. G. Pyne, *Sulfur Reports* 1992, 12, 57; (b) C. R. Johnson, *Aldrichchimica Acta* 1985, 18, 3). The production of enantiomer-pure sulfoximines is described, e.g., via the racemate cleavage with enantiomer-pure camphor-10-sulfonic acid ((a) C. R. Johnson, C. W. Schroeck, *J. Am. Chem. Soc.* 1973, 95, 7418; (b) C. S. Shiner, A. H. Berks, *J. Org. Chem.* 1988, 53, 5543). Another method for producing optically active sulfoximines consists in the stereoselective imination of optically active sulfoxides with use of MSH ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239) or trifluoroacetamide, iodobenzene diacetate, magnesium oxide and [Rh₂(OAc)₄] (H. Okamura and C. Bolm, *Org. Lett.* 2004, 6, 1305).

The following examples explain the production of the compounds according to the invention without limiting the scope of the claimed compounds to these examples.

General Procedure for the Synthesis of Compounds According to the Invention

Scheme 1

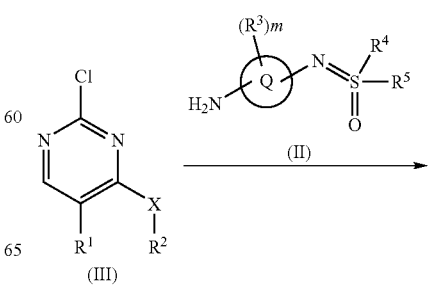

-continued

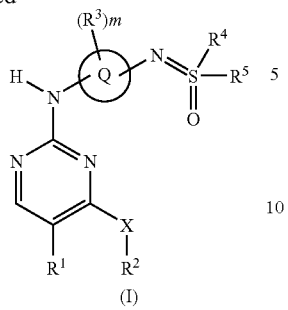

The substituents Q, X, R¹, R², R³, R⁴, R⁵ and m have the meanings which are indicated in any one of claims 1 to 19.

a) Production of Intermediates a₁) General Procedures for the Synthesis of Intermediates of General Formula (II):

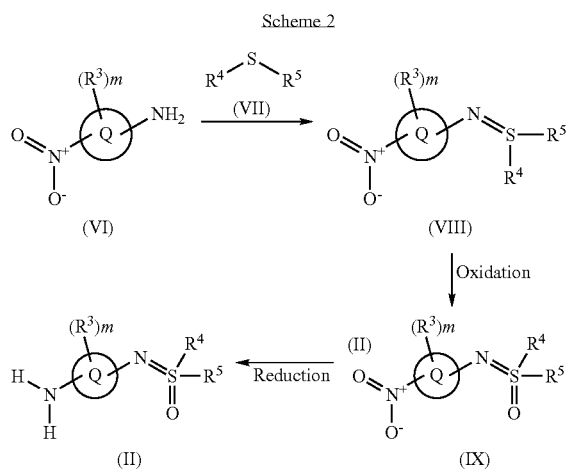

The substituents Q, R³, R⁴, R⁵ and m have the meanings which are indicated in any one of claims 1 to 19.

Compounds of general formula (VI) may be reacted with thioethers of general formula (VII) to give intermediates of general formula (VIII). (see for examples: a) D. Swern et al in *J. Org. Chem.* 1977, 42, 592-597; b) E. Jäger et al in *Monatsheft Chemie* 1985, 116, 1153-1164; c) J. Bailer et al in *Tetrahedron* 1980, 36, 901-911; d) Silbernagel et al in *Monatsheft Chemie* 1985, 116, 841-850; e) Alexis et al in *Monatsheft Chemie* 1985, 116, 413-416; f) E. Jäger et al in *Monatsheft Chemie* 1985, 116, 1017-1026; g) T. L. Gilchrist et al in *J. Chem. Soc. Perkin Trans.* 1 1975, 1969-1973; h) M. Sakamato et al in *Chem. Pharm. Bull.* 1979, 2116-2121).

Intermediates of general formula (VIII) may then be oxidised to give intermediates of general formula (IX) (see for examples: a) D. Swern et al in *J. Org. Chem.* 1979, 44, 2510-2513, b) P. K. Claus et al in *Tetrahedron Lett.* 1974, 3319-3322; c) A. Defoin et al in *Helv. Chim. Acta* 1989, 1199-1215; d) E. Jäger et al in *Monatsheft Chemie* 1985, 116, 1153-1164; e) M. D. Coburn in *J. Heterocycl. Chem.* 1989, 26, 1883-1884).

Finally, the nitro group of intermediates of general formula (IX) is reduced to give intermediates of general formula (II). For the reduction of a nitro group there are a plethora of methods available (see for example: R. C. Larock, Comprehensive Organic Transformations, VCH, New York, 1989, 411-415). Preferentially, intermediates of general formula (IX) are hydrogenated using palladium on charcoal as a catalyst.

Alternative procedure for the synthesis of intermediates of general formula (IX)

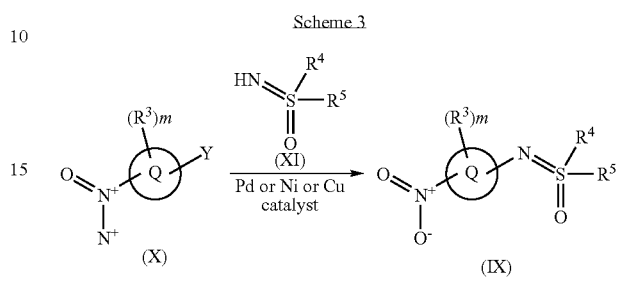

The substituents Q, R³, R⁴, R⁵ and m have the meanings which are indicated in any one of claims 1 to 19. For the meaning of Y refer to text below.

Another possibility to prepare intermediates of general formula (IX), which may then be reduced to intermediates of general formula (II), is described in scheme 3. By means of palladium-, nickel- or copper-catalyzed cross-coupling reactions, sulfoximines of gernal formula (XI) may be reacted with compounds of general formula (X) to give intermediates of general formula (IX) (for Y=Br or I see: (a) C. Bolm et al, *Tetrahedron Lett.* 1998, 39, 5731-5734; b) M. Harmata et al, *Angew. Chemie* 1999, 38, 2577-2579; c) C. Bolm, J. P. Hildebrandt, *J. Org. Chem.* 2000, 65, 169; d) M. Ghosh et al., *Org. Lett.* 2001, 3, 3321-3324, e) C. Bolm, M. Verrucci, O. Simic, P. G. Cozzi, G. Raabe, H. Okamura, *Chem. Commun.* 2003, 22, 2826-2827; f) E. Magnier, *Synthesis* 2003, 565-569; g) M. Harmata et al, *J. Am. Chem. Soc* 2003, 125, 5754-5756; h) G. Y. Cho, P. Rémy, J. Jansson, C. Moessner, C. Bolm, *Org. Lett.* 2004, 6, 3293-3296; i) C. Bolm et al, *J. Org. Chem.* 2005, 70, 2346-2349; j) Bolm et al, *Syn. Lett.* 2005, 781-784; for Y=sulfonates see k) C. Bolm et al. *Synthesis* 2000, 911-913).

a₂) General Procedure for the Synthesis of Intermediates of General Formula (III):

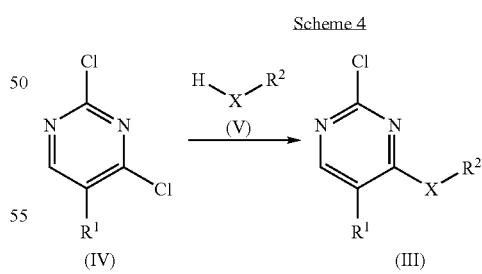

The substituents R¹, R² and X have the meaning which are indicated in any one of claims 1 to 19.

2,4-Dichloro-pyrimidines of general formula (IV) can be reacted with nucleophiles of general formula (V) to give intermediates of general formula (III) (see for examples: a) U. Lücking et al, WO 2005037800; b) J. Bryant et al, WO 2004048343; c) U. Lücking et al, WO 2003076437; d) T. Brumby et al, WO 2002096888).

b) Production of End Products

According to general procedure (scheme 1) intermediates of general formula (II) and (III) are coupled under acidic conditions to give a compound of general formula (I). Suitable acids include for example hydrogen chloride. Suitable solvents which may be mentioned are polar organic solvents like acetonitrile, isopropanol, butanol or DMF, solvent mixtures of organic solvents or mixtures of polar organic solvents with water. The reaction is carried out at a temperature in the range of room temperature to reflux, depending on the reactivity of the intermediates of general formula (II) and (III), the nature of the employed acid and/or solvents or solvent mixtures. For the use of isopropanol, acetonitrile and acetonitrile/water mixtures in combination with hydrogen chloride the reaction is preferentially carried out in the range of 60° C. to 80° C.

EXAMPLE 1

N-{4-[(5-Bromo-4-{[(R)-2-hydroxy-1,2-dimethylpropyl]amino}-pyrimidin-2-yl)amino]phenyl}-S,S-dimethylsulfoximide

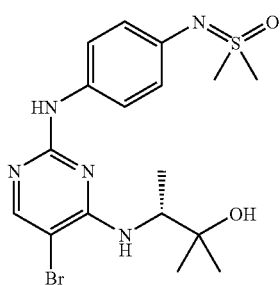

1a) Production of Intermediates

Intermediate 1.1

N-(4-Nitrophenyl)-S,S-dimethyliminosulfurane

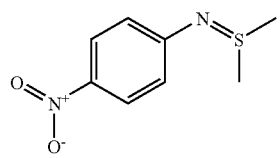

The compound is prepared according to the published procedure of D. Swern et al in *J. Org. Chem.* 1977, 42, 592-597.

$^1$H-NMR (DMSO): 7.88 (m, 2H), 6.64 (m, 2H), 2.79 (s, 6H).

Intermediate 1.2

S,S-Dimethyl-N-(4-nitrophenyl)sulfoximide

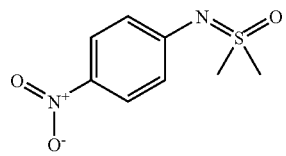

The compound is prepared according to the published procedure of D. Swern et al in *J. Org. Chem.* 1979, 44, 2510-2513 starting with intermediate 1.1.

$^1$H-NMR (DMSO): 8.06 (m, 2H), 7.05 (m, 2H), 3.38 (s, 6H).

MS: 215 (ES).

Intermediate 1.3

N-(4-Aminophenyl)-S,S-dimethylsulfoximide

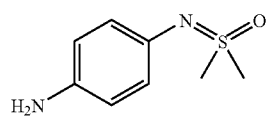

A solution of 214 mg (1.00 mmol) of intermediate 1.2 (S,S-Dimethyl-N-(4-nitrophenyl)sulfoximide) in 20 ml of ethanol is hydrogenated at room temperature with use of 40 mg of Pd/C (10%×50% H$_2$O) under a hydrogen atmosphere at normal pressure over 45 minutes. The hydrogen absorption is 74 ml. The batch is filtered and concentrated by evaporation. 160 mg (0.87 mmol, corresponding to 87% of theory) of the product is obtained.

$^1$H-NMR (DMSO): 6.64 (m, 2H), 6.42 (m, 2H), 4.60 (br, 2H), 3.06 (s, 6H).

MS: 185 (ES).

Intermediate 1.4 methyl-N-(5-bromo-2-chloropyrimidin-4-yl)-D-alaninate

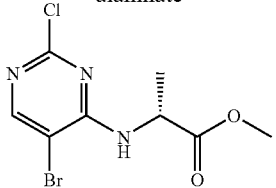

22.8 g (100 mmol) of 5-bromo-2,4-dichloropyrimidine and 14.0 g (100 mmol) of D-alanic acid methyl ester hydrochloride are dissolved in 300 ml of THF and 75 ml of DMF. The ice-cooled batch is mixed with 33.5 ml (240 mmol) of triethylamine and then slowly heated to room temperature. After 48 hours, the solvent is drawn off in a rotary evaporator, and the remaining residue is purified by chromatography (hexane/ethyl acetate: 4:1-2:1). 25.5 g (86.1 mmol, corresponding to 86% of theory) of the product is obtained.

$^1$H-NMR (CDCl$_3$): 8.2 (s, 1H), 6.1 (d, 1H), 4.8 (m, 1H), 3.8 (s, 3H), 1.6 (d, 3H).

Intermediate 1.5

(R)-3-[(5-bromo-2-chloropyrimidin-4-yl)amino]-2-methyl-butan-2-ol

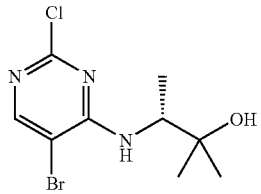

An ice-cooled solution of 2.95 g (10.0 mmol) of intermediate 1.4 (methyl-N-(5-bromo-2-chloropyrimidin-4-yl)-D-alaninate) in 150 ml of THF is mixed drop by drop with 30 ml (90 mmol) of a 3 molar solution of methylmagnesium bromide in diethyl ether. After 2.5 hours at room temperature, the batch is mixed with 30 ml of saturated ammonium chloride solution. It is diluted with water and extracted from ethyl acetate (3×). The combined organic phases are dried (Na$_2$SO$_4$), filtered and concentrated by evaporation. The remaining residue is purified by chromatography (hexane/ethyl acetate: 4:1-1:1). 2.81 g (9.5 mmol, corresponding to 95% of theory) of the product is obtained.

$^1$H-NMR (CDCl$_3$): 8.1 (s, 1H), 5.9 (d, 1H), 4.2 (m, 1H), 1.8 (br, 1H), 1.2 (m, 9H).

1b) Production of End Product 155 mg (0.84 mmol) of intermediate 1.3 (N-(4-Aminophenyl)-S,S-dimethylsulfoximide) and 269 mg (0.91 mmol) of intermediate 1.5 ((R)-3-(5-Bromo-2-chloro-pyrimidin-4-ylamino)-2-methyl-butan-2-ol) in 5.00 ml of acetonitrile and 0.50 ml of water are mixed with 0.25 ml of a 4N solution of HCl in dioxane. The batch is stirred for 16 hours at 60° C. and then is diluted with ethyl acetate. After the addition of NaHCO$_3$ solution the batch is extracted with ethyl acetate (3×). The combined organic phases are dried (Na$_2$SO$_4$), filtered and concentrated by evaporation. The remaining residue is purified by chromatography (DCM/EtOH 9:1). 115 mg (0.27 mmol, corresponding to 32% of theory) of the product is obtained.

$^1$H-NMR (DMSO): 8.98 (s, 1H), 7.99 (s, 1H), 7.48 (m, 2H), 6.82 (m, 2H), 5.93 (d, 1H), 4.79 (s, 1H), 4.05 (m, 1H), 3.14 (s, 6H), 1.15 (m, 9H).

MS: 442 (ES).

EXAMPLE 2

N-{4-[(5-Bromo-4-{[(1R,2R)-2-hydroxy-1-methylpropyl]amino}-pyrimidin-2-yl)amino]phenyl}-S,S-dimethylsulfoximide

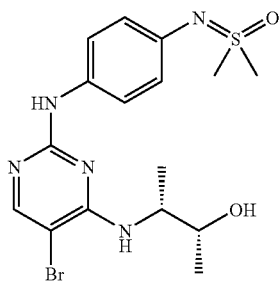

2a) Production of Intermediates

Intermediate 2.1

(R)-2-[(5-bromo-2-chloropyrimidin-4-yl)amino]propanal

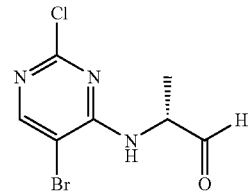

A solution of 40.0 g (135.8 mmol) of intermediate 1.4 (methyl-N-(5-bromo-2-chloropyrimidin-4-yl)-D-alaninate, example 1) in 800 ml of toluene is mixed at −78° C. with 310 ml of a 1.2 molar solution of diisobutyl aluminum hydride. After 30 minutes, it is carefully quenched with methanol. The batch is heated to room temperature and diluted with 1000 ml of tert-butyl methyl ether. It is washed successively with 1 N HCl (3×100 ml), saturated sodium bicarbonate solution (3×) and saturated NaCl solution (3×). The organic phase is dried (MgSO$_4$), filtered and concentrated by evaporation. The remaining residue is purified by chromatography (hexane/ethyl acetate: 4:1-1:1). 22.5 g (83.9 mmol, corresponding to 62% of theory) of the product is obtained.

$^1$H-NMR (CDCl$_3$): 9.6 (s, 1H), 8.2 (s, 1H), 6.3 (d, 1H), 4.8 (m, 1H), 1.5 (d, 3H).

Intermediate 2.2

(2R,3R)-3-[(5-bromo-2-chloropyrimidin-4-yl)amino]butan-2-ol

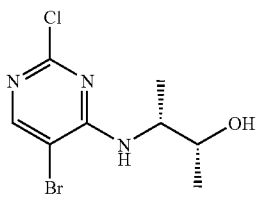

32.7 g (159 mmol) of copper(I)bromide dimethyl sulfide complex is introduced under nitrogen atmosphere into 1000 ml of diethyl ether and cooled to −78° C. Over a period of about 25 minutes, 200 ml of a 1.6 molar solution of methyllithium in diethyl ether is added in drops, and then the cooling bath is removed. The batch is stirred for 40 minutes, and the temperature increases to −35° C. It is cooled to −55° C., and 18.9 g (71.5 mmol) of (R)-2-[(5-bromo-2-chloropyrimidin-4-yl)amino]propanal is added over a period of 20 minutes. It is stirred for 6 hours at −55° C., then the cooling bath is filled with dry ice again, covered with aluminum foil, and the batch is stirred overnight. 200 ml of a saturated ammonium chloride solution is added in drops, and the batch is heated to room temperature. It is diluted with 500 ml of diethyl ether, the organic phase is separated, and the aqueous phase is extracted with diethyl ether. The combined organic phases are washed with saturated ammonium chloride solution and saturated NaCl solution, dried (Na$_2$SO$_4$), filtered and concentrated by evaporation. The remaining residue is purified by chromatography (hexane/ethyl acetate: 4:1-1:1). 8.4 g (30.0 mmol, corresponding to 42% of theory) of the product is obtained.

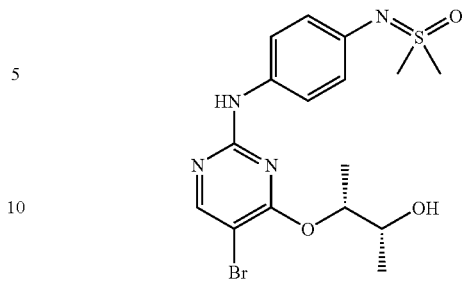

3a) Production of Intermediates

Intermediate 3.1

(2R,3R)-3-[(5-bromo-2-chloropyrimidin-4-yl)oxy]-butan-2-ol

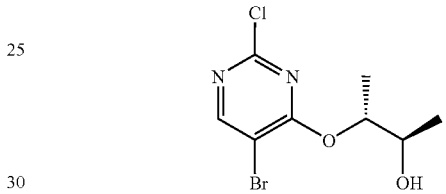

A solution of 1.35 g (15.0 mmol) of (R,R)-(−)-2,3-butanediol in 50 ml of THF is mixed at 0° C. in portions with 480 mg (11.0 mmol) of sodium hydride (55% dispersion) and then stirred for 10 minutes at room temperature. The solution that is produced is added at 0° C. to 2.27 g (10.0 mmol) of 5-bromo-2,4-dichloropyrimidine in 25 ml of THF. The batch is slowly heated to room temperature and stirred for 12 hours. The solvent is drawn off, and the residue that is obtained is purified by chromatography (hexane/ethyl acetate 1:1). 2.29 g (8.1 mmol, corresponding to 81% of theory) of the product is obtained.

$^1$H-NMR (DMSO): 8.44 (s, 1H), 5.18 (q, 1H), 3.96 (q, 1H), 2.02 (d, 1H), 1.4 (d, 3H), 1.28 (d, 3H).

MS: 281 (ES).

3b) Production of End Product 83 mg (0.45 mmol) of intermediate 1.3 (N-(4-Aminophenyl)-S,S-dimethylsulfoximide, example 1) and 140 mg (0.91 mmol) of intermediate 3.1 ((2R,3R)-3-(5-Bromo-2-chloropyrimidin-4-yloxy)-butan-2-ol) in 3.00 ml of acetonitrile and 0.20 ml of water are mixed with 0.14 ml of a 4N solution of HCl in dioxane. The batch is stirred for 25 hours at 60° C. and then is diluted with ethyl acetate. After the addition of NaHCO$_3$ solution the batch is extracted with ethyl acetate (3×). The combined organic phases are dried (Na$_2$SO$_4$), filtered and concentrated by evaporation. The remaining residue is purified by chromatography (DCM/EtOH 9:1). 21 mg (0.05 mmol, corresponding to 11% of theory) of the product is obtained.

$^1$H-NMR (DMSO): 9.39 (s, 1H), 8.22 (s, 1H), 7.42 (d, 2H), 6.79 (d, 2H), 5.13 (m, 1H), 4.81 (d, 1H), 3.76 (m, 1H), 3.12 (s, 6H), 1.22 (d, 3H), 1.07 (d, 3H).

MS: 429 (ES).

EXAMPLE 4

---

$^1$H-NMR (CDCl$_3$): 8.1 (s, 1H), 5.8 (d, 1H), 4.2 (m, 1H), 3.9 (m, 1H), 2.0 (d, 1H), 1.3 (d, 3H), 1.2 (d, 3H).

HPLC Analysis:
Column: Chiralpak AD-H 5μ
Length×ID: 150×4.6 mm
Eluants: A=Hexane, C=Ethanol
Flow: 1.0 ml/min
Gradient: Isocratic 5% C
Detector: UV 254 nm
Temperature: 25° C.
RT in min: 6.04

2b) Production of End Product 83 mg (0.45 mmol) of intermediate 1.3 (N-(4-Aminophenyl)-S,S-dimethylsulfoximide, example 1) and 140 mg (0.54 mmol)) of intermediate 2.2 ((2R,3R)-3-(5-Bromo-2-chloropyrimidin-4-ylamino)-butan-2-ol) in 3.00 ml of acetonitrile and 0.20 ml of water are mixed with 0.14 ml of a 4N solution of HCl in dioxane. The batch is stirred for 22 hours at 60° C. The solvent is drawn off, and the remaining residue is purified by chromatography (DCM/EtOH 9:1). 43 mg (0.10 mmol, corresponding to 22% of theory) of the product is obtained.

$^1$H-NMR (DMSO): 8.97 (s, 1H), 7.94 (s, 1H), 7.44 (d, 2H), 6.77 (d, 2H), 5.88 (d, 1H), 4.96 (d, 1H), 4.00 (m, 1H), 3.69 (m, 1H), 3.11 (s, 6H), 1.15 (d, 3H), 1.04 (d, 3H).

MS: 428 (ES).

EXAMPLE 3

N-{4-[(5-Bromo-4-{[(1R,2R)-2-hydroxy-1-methylpropyl]oxy}-pyrimidin-2-yl)amino]phenyl}S,S-dimethylsulfoximide N-{4-[(4-{[(R)-1-(Hydroxymethyl)-2-methylpropyl]amino}-5-iodopyrimidin-2-yl) amino]phenyl}-S,S-dimethylsulfoximide

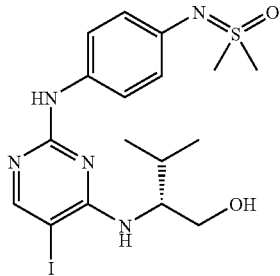

4a) Production of Intermediates

Intermediate 4.1

(R)-2-(2-Chloro-5-iodo-pyrimidin-4-ylamino)-3-methyl-butan-1-ol

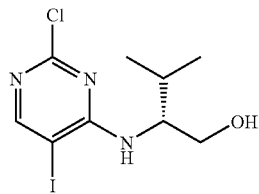

A solution of 10.05 g (36.6 mmol) of 2,4-Dichloro-5-iodo-pyrimidine and 5.6 ml (40.0 mmol) triethylamine in 30 ml of acetonitrile is mixed with 4.85 g (47.0 mmol) of (R)-2-Amino-3-methyl-butan-1-ol. The batch is stirred at room temperature for 16 hours and is finally diluted with water. The batch is filtered and the solid is washed with small amounts of acetonitrile and water. The solid is dried. 10.24 g (30.0 mmol, corresponding to 82% of theory) of the product is obtained.

$^1$H-NMR (DMSO-D6): 8.35 (s, 1H), 6.39 (d, 1H), 4.82 (tr, 1H), 3.92 (m, 1H), 3.55 (m, 2H), 1.97 (m, 1H), 0.92 (d, 3H), 0.88 (d, 3H).

MS: 341 (EI).

4b) Production of End Product 300 mg (1,63 mmol) of intermediate 1.3 (N-(4-Aminophenyl)-S,S-dimethylsulfoximide, example 1) and 556 mg (1,63 mmol) of intermediate 4.1 ((R)-2-(2-Chloro-5-iodo-pyrimidin-4-ylamino)-3-methyl-butan-1-ol) in 9.00 ml of acetonitrile and 0.60 ml of water are mixed with 0.41 ml of a 4N solution of HCl in dioxane. The batch is stirred for 7 hours at 60° C. and then is diluted with ethyl acetate. After the addition of NaHCO$_3$ solution the batch is extracted with ethyl acetate (3×). The combined organic phases are dried (Na$_2$SO$_4$), filtered and concentrated by evaporation. The remaining residue is purified by chromatography (DCM/EtOH 9:1). 225 mg (0.46 mmol, corresponding to 28% of theory) of the product is obtained.

$^1$H-NMR (DMSO-D6): 8.91 (s, 1H), 8.04 (s, 1H), 7.45 (m, 2H), 6.76 (m, 2H), 5.63 (d, 1H), 4.78 (tr, 1H), 3.94 (m, 1H), 3.57 (m, 1H), 3.45 (m, 1H), 3.11 (s, 6H), 1.95 (m, 1H), 0.88 (m, 6H).

MS: 489 (EI).

EXAMPLE 5

N-[4-({5-Bromo-4-[(6-methyl-2-pyridyl)amino]pyrimidin-2-yl}amino)phenyl]-S,S-dimethylsulfoximide

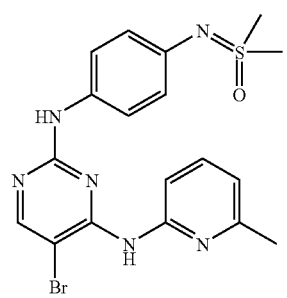

5a) Production of Intermediates

Intermediate 5.1

5-Bromo-2-chloro-pyrimidin-4-yl)-(6-methyl-pyridin-2-yl)-amine

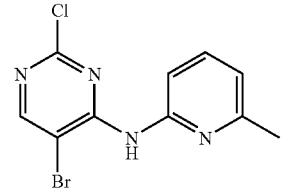

A solution of 2.62 g (14.5 mmol) of 5-Bromo-2,4-dichloropyrimidine and 2.5 ml (14.5 mmol) of N,N-diisopropylethylamine in 40 ml of n-butanol is mixed with 1.57 g (14.5 mmol) of 2-amino-6-methylpyridine. The batch is refluxed for 4 hours and finally concentrated by evaporation. The remaining residue is purified by chromatography (hexane/ethyl acetate: 7:3). 602 mg (2.0 mmol, corresponding to 14% of theory) of the product is obtained.

$^1$H-NMR (DMSO-D6): 8.88 (m, 1H), 8.08 (s, 1H), 7.78 (m, 2H), 7.06 (m, 1H), 2.45 (s, 3H).

5b) Production of End Product 80 mg (0,43 mmol) of intermediate 1.3 (N-(4-Aminophenyl)-S,S-dimethylsulfoximide, example 1) and 130 mg (0,43 mmol) of intermediate 5.1 ((5-Bromo-2-chloro-pyrimidin-4-yl)-(6-methyl-pyridin-2-yl)-amine) in 3.00 ml of acetonitrile and 0.20 ml of water are mixed with 0.11 ml of a 4N solution of HCl in dioxane. The batch is stirred for 7 hours at 60° C. and then is diluted with ethyl acetate. The batch is filtered and the solid is washed with ethyl acetate. The solid is dissolved in DCM/MeOH (1:1) and concentrated by evaporation. The remaining residue is purified by chromatography (DCM/EtOH 9:1). 28 mg (0.06 mmol, corresponding to 14% of theory) of the product is obtained.

$^1$H-NMR (DMSO-D6): 9.29 (s, 1H), 8.22 (s, 1H), 8.02 (m, 2H), 7.61 (m, 1H), 7.36 (m, 2H), 6.95 (m, 1H), 6.81 (m, 2H), 3.12 (s, 6H), 2.38 (s, 3H).

MS: 446 (EI).

EXAMPLE 6

N-{4-[(4-Anilino-5-bromopyrimidin-2-yl)amino]phenyl}-S,S-dimethylsulfoximide

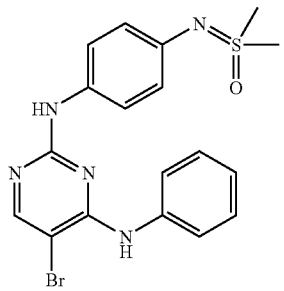

6a) Production of Intermediates

Intermediate 6.1

(5-Bromo-2-chloro-pyrimidin-4-yl)-phenyl-amine

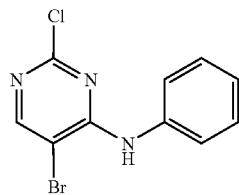

A solution of 11.8 g (52.0 mmol) of 5-Bromo-2,4-dichloropyrimidine in 10 ml of acetonitrile at 0° C. is mixed with 4.73 ml (52.0 mmol) of aniline. The batch is stirred for 3 days at room temperature and finally concentrated by evaporation. The remaining residue is purified by chromatography (hexane/ethyl acetate: 3:1 plus 1% triethylamine). 4.94 g (17.4 mmol, corresponding to 33% of theory) of the product is obtained.

$^1$H-NMR (DMSO-D6): 9.29 (s, 1H), 8.45 (s, 1H), 7.52 (m, 2H), 7.40 (m, 2H), 7.19 (m, 1H),

MS: 284 (CI)

6b) Production of End Product 80 mg (0,43 mmol) of intermediate 1.3 (N-(4-Aminophenyl)-S,S-dimethylsulfoximide, example 1) and 123 mg (0,43 mmol) of intermediate 6.1 ((5-Bromo-2-chloro-pyrimidin-4-yl)-phenyl-amine) in 3.00 ml of acetonitrile and 0.20 ml of water are mixed with 0.11 ml of a 4N solution of HCl in dioxane. The batch is stirred for 7 hours at 60° C. and then is diluted with ethyl acetate. The batch is filtered and the solid is washed with ethyl acetate. The solid is dissolved in DCM/MeOH (1:1) and concentrated by evaporation. The remaining residue is purified by chromatography (DCM/EtOH 9:1). 34 mg (0.08 mmol, corresponding to 18% of theory) of the product is obtained.

$^1$H-NMR (DMSO-D6): 9.06 (s, 1H), 8.48 (s, 1H), 8.12 (s, 1H), 7.58 (m, 2H), 7.30 (m, 4H), 7.07 (m, 1H), 6.70 (m, 2H), 3.11 (s, 6H).

MS: 431 (EI).

EXAMPLE 7

N-{4-[(4-{[(R)-2-Hydroxy-1-methylethyl]amino}-5-nitropyrimidin-2-yl)amino]phenyl}-S,S-dimethylsulfoximide

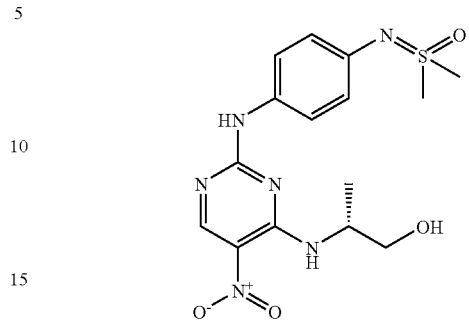

7a) Production of Intermediates

Intermediate 7.1

(R)-2-(2-Chloro-5-nitro-pyrimidin-4-ylamino)-propan-1-ol

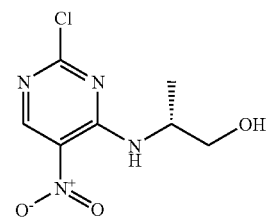

A solution of 315 mg (4.2 mmol) of (R)-2-Amino-propan-1-ol in 5 ml of acetonitrile is added slowly to a suspension of 388 mg (2.0 mmol) of 2,4-dichloro-5-nitro-pyrimidine in 20 ml acetonitrile at −30° C. to −20° C. The batch is stirred for 3 hours at −30° C. to −20° C. The batch is diluted with ethylacetate and ice water. The batch is extracted with ethyl acetate (3×). The combined organic phases are washed with NaCl solution, dried (Na$_2$SO$_4$), filtered and concentrated by evaporation. 350 mg (1.51 mmol, corresponding to 76% of theory) of the product is obtained.

$^1$H-NMR (DMSO-D6): 9.01 (s, 1H), 8.65 (d, 1H), 4.35 (m, 1H), 3.47 (m, 2H), 1.35 (d, 3H).

MS: 233 (ESI).

7b) Production of End Product 95 mg (0,52 mmol) of intermediate 1.3 (N-(4-Aminophenyl)-S,S-dimethylsulfoximide, example 1) and 120 mg (0,52 mmol) of intermediate 7.1 ((R)-2-(2-Chloro-5-nitro-pyrimidin-4-ylamino)-propan-1-ol) in 3.6 ml of acetonitrile and 0.24 ml of water are mixed with 0.13 ml of a 4N solution of HCl in dioxane. The batch is stirred for 3 hours at 60° C. and then diluted with NaHCO$_3$ solution and NaCl solution. The batch is extracted with ethyl acetate (3×). The combined organic phases are dried (Na$_2$SO$_4$), filtered and concentrated by evaporation. The remaining residue is purified by chromatography (DCM/EtOH 95:5). 48 mg (0.13 mmol, corresponding to 24% of theory) of the product is obtained.

$^1$H-NMR (DMSO-D6): 10.21 (s, 1H), 8.91 (s, 1H), 8.61 (br, 1H), 7.55 (m, 2H), 6.83 (m, 2H), 5.04 (tr, 1H), 4.28 (m, 1H), 3.51 (m, 2H), 3.15 (s, 6H), 1.21 (d, 3H).

MS: 381 (ES).

EXAMPLE 8

N-[4-({5-Bromo-4-[(3-hydroxypropyl)sulfanyl]pyrimidin-2-yl}amino)phenyl]-S,S-dimethylsulfoximide

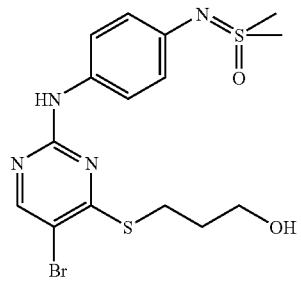

8a) Production of Intermediates

Intermediate 8.1

3-(5-Bromo-2-chloro-pyrimidin-4-ylsulfanyl)-propan-1-ol

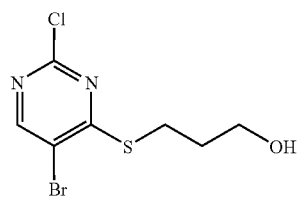

A solution of 2.47 g (10.8 mmol) of 5-Bromo-2,4-dichloropyrimidine in 30 ml of acetonitrile at −20° C. is mixed with 1.5 ml (10.8 mmol) of triethylamine and 1.00 g (10.8 mmol) of 3-Mercapto-propan-1-ol. The batch is slowly warmed to room temperature and stirred for 16 hours. The batch is filtrated to remove the solid precipitate. The filtrate is concentrated by evaporation. 2-Methoxy-2-methyl-propane is added to the remaining residue and the batch is stirred for 15 minutes. The batch is filtrated and the solid precipitate is dried. 3.03 g (10.6 mmol, corresponding to 98% of theory) of the product is obtained.

$^1$H-NMR (DMSO-D6): 8.65 (s, 1H), 4.63 (br, 1H), 3.50 (m, 2H), 3.18 (tr, 1H), 1.81 (m, 2H).

MS: 283 (ES).

8b) Production of End Product 180 mg (0,98 mmol) of intermediate 1.3 (N-(4-Aminophenyl)-S,S-dimethylsulfoximide, example 1) and 304 mg (1,07 mmol) of intermediate 8.1 (3-(5-Bromo-2-chloro-pyrimidin-4-ylsulfanyl)-propan-1-ol) in 14.5 ml of isopropanole are mixed with 0.05 ml of a 4N solution of HCl in dioxane. The batch is stirred for 60 hours at 70° C. and then concentrated by evaporation. The remaining residue is purified by HPLC. 7 mg (0.02 mmol, corresponding to 2% of theory) of the product is obtained.

Column: XBridge C18 5µ 150×19 mm
Solvent: A: H$_2$O B: Acetonitril
Buffer: A/0,2% NH$_3$
Gradient: 76% A+24% B(1')__24->38% B(10')__38->95% B(0,5')
Flow: 20,0 mL/min
Solution: 31 mg/2,0 mL DMSO/CH$_3$OH 1:1
Injection Volume: 1×2,0 mL
Detection: DAD (200-500 nm) TIC; MS-ESI+(120-1000 m/z) TIC
Temperature: Rt
Retention time: 10.0-10.4 min $^1$H-NMR (DMSO-D6): 9.48 (s, 1H), 8.19 (s, 1H), 7.42 (m, 2H), 6.81 (m, 2H), 4.55 (tr, 1H), 3.45 (m, 2H), 3.30 (m, 2H), 3.14 (s, 6H), 1.78 (m, 2H).

EXAMPLE 9

S,S-Dimethyl-N-(4-{[4-(prop-2-yn-1-yloxy)-5-(trifluoromethyl)pyrimidin-2-yl]amino}phenyl)sulfoximide

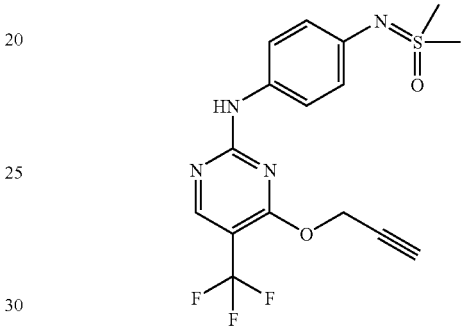

9a) Production of Intermediates

Intermediate 9.1

2-Chloro-4-prop-2-ynyloxy-5-trifluoromethyl-pyrimidine

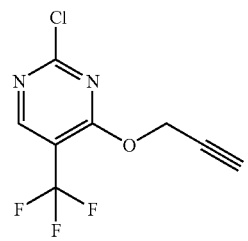

3.97 ml (68.2 mmol) Prop-2-yn-1-ol are slowly added to 3.40 g (15.6 mmol) of 2,4-Dichloro-5-trifluoromethyl-pyrimidine at 0° C. under a nitrogen atmosphere. 0.79 ml Trifluoro-acetic acid are added dropwise and the batch is stirred for 6 hours at 0° C. The batch is poured on ice and extracted with ethyl acetate (3×). The combined organic phases are washed with water, dried (Na$_2$SO$_4$), filtered and concentrated by evaporation. The remaining residue is purified by chromatography (hexane/ethyl acetate 95:5). 591 mg (2.5 mmol, corresponding to 16% of theory) of the product is obtained.

$^1$H-NMR (CDCl$_3$): 8.61 (s, 1H), 5.16 (d, 2H), 2.57 (tr, 1H).
MS: 236 (EI).

9b) Production of End Product 132 mg (0,72 mmol) of intermediate 1.3 (N-(4-Aminophenyl)-S,S-dimethylsulfoximide, example 1) and 170 mg (1,63 mmol) of intermediate 9.1 (2-Chloro-4-prop-2-ynyloxy-5-trifluoromethyl-pyrimidine) in 5.00 ml of acetonitrile and 0.33 ml of water are mixed with 0.18 ml of a 4N solution of HCl in dioxane. The batch is stirred for 3 hours at 60° C. and then concentrated by evaporation. The remaining residue is purified by chromatography (DCM/EtOH 85:15). 44 mg (0.11 mmol, corresponding to 15% of theory) of the product is obtained.

$^1$H-NMR (DMSO-D6): 10.05 (br, 1H), 8.47 (s, 1H), 7.52 (m, 2H), 6.85 (m, 2H), 5.08 (br, 2H), 3.62 (tr, 1H), 3.14 (s, 6H).

MS: 385 (ES+).

EXAMPLE 10

S,S-Dimethyl-N-(4-{[4-(prop-2-yn-1-ylamino)-5-(trifluoromethyl)pyrimidin-2-yl]amino}phenyl)sulfoximide

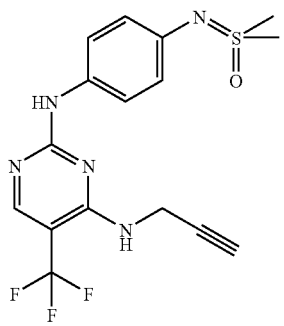

10a) Production of Intermediates

Intermediate 10.1

(2-Chloro-5-trifluoromethyl-pyrimidin-4-yl)-prop-2-ynyl-amine

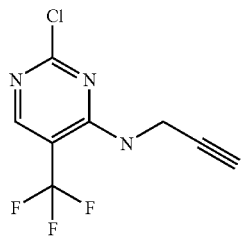

The compound was prepared according to J. Bryant et al, WO 2004/048343, page 74.

10b) Production of End Product 96 mg (0,52 mmol) of intermediate 1.3 (N-(4-Aminophenyl)-S,S-dimethylsulfoximide, example 1) and 123 mg (0,52 mmol) of intermediate 10.1 ((2-Chloro-5-trifluoromethyl-pyrimidin-4-yl)-prop-2-ynyl-amine) in 3.60 ml of acetonitrile and 0.24 ml of water are mixed with 0.13 ml of a 4N solution of HCl in dioxane. The batch is stirred for 90 minutes at 60° C. and then concentrated by evaporation. The remaining residue is purified by chromatography (DCM/EtOH 85:15). 98 mg (0.26 mmol, corresponding to 50% of theory) of the product is obtained.

$^1$H-NMR (DMSO-D6): 9.48 (br, 1H), 8.13 (s, 1H), 7.55 (m, 2H), 7.41 (br, 1H), 6.78 (m, 2H), 4.08 (m, 2H), 3.13 (s, 6H), 3.08 (tr, 1H).

MS: 384 (ES+).

EXAMPLE 11

N-{4-[(5-Bromo-4-{[1-(hydroxymethyl)cyclopentyl]amino}pyrimidin-2-yl)amino]phenyl}-S,S-dimethyl-sulfoximide

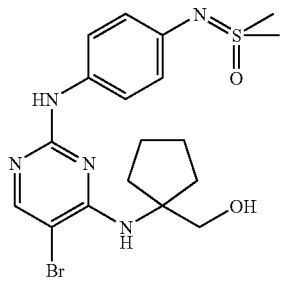

11a) Production of Intermediates

Intermediate 11.1

[1-(5-Bromo-2-chloro-pyrimidin-4-ylamino)-cyclopentyl]-methanol

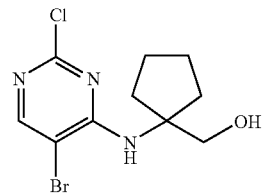

An ice-cooled solution of 2.28 g (10.0 mmol) of 5-Bromo-2,4-dichloropyrimidine and 1.7 ml (12.0 mmol) of triethylamine in 10 ml of acetonitrile is mixed with 1.38 g (12.0 mmol) (1-amino-cyclopentyl)-methanol. After 16 hours at room temperature the batch is filtrated to remove the solid precipitate. The precipitate is dried. 1.48 g (4.8 mmol, corresponding to 48% of theory) of the product is obtained.

$^1$H-NMR (DMSO-D6): 8.26 (s, 1H), 6.38 (s, 1H), 5.19 (tr, 1H), 3.52 (d, 2H), 2.01 (m, 2H), 1.72 (m, 4H), 1.53 (m, 2H).

11b) Production of End Product 95 mg (0,52 mmol) of intermediate 1.3 (N-(4-Aminophenyl)-S,S-dimethylsulfoximide, example 1) and 158 mg (0,52 mmol) of intermediate 11.1 ([1-(5-Bromo-2-chloro-pyrimidin-4-ylamino)-cyclopentyl]-methanol) in 3.60 ml of acetonitrile and 0.24 ml of water are mixed with 0.13 ml of a 4N solution of HCl in dioxane. The batch is stirred for 3 hours at 60° C. An additional amount of 47 mg (0,26 mmol) of intermediate 1.3 (N-(4-Aminophenyl)-S,S-dimethylsulfoximide, example 1) is added and the batch is stirred for 10 hours at 60° C. The batch is concentrated by evaporation. The remaining residue is purified by chromatography (DCM/EtOH 85:15). 66 mg (0.15 mmol, corresponding to 28% of theory) of the product is obtained.

¹H-NMR (DMSO-D6): 8.79 (s, 1H), 7.90 (s, 1H), 7.32 (m, 2H), 6.78 (m, 2H), 5.55 (s, 1H), 4.92 (tr, 1H), 3.53 (br, 2H), 3.11 (s, 6H), 2.04 (m, 2H), 1.63 (m, 4H), 1.48 (m, 2H).
MS: 454 (ES+).

EXAMPLE 12

N-{4-[(5-Bromo-4-{[(1S,2S)-2-hydroxycyclohexyl]amino}pyrimidin-2-yl)amino]phenyl}S,S-dimethylsulfoximide

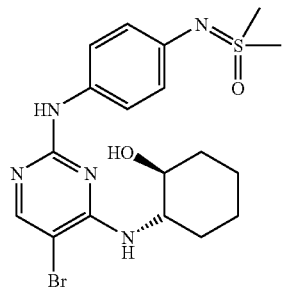

12a) Production of Intermediates

Intermediate 12.1 trans-2-(5-Bromo-2-chloro-pyrimidin-4-ylamino)-cyclohexanol

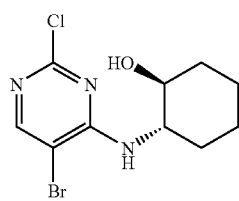

An ice-cooled solution of 2.28 g (10.0 mmol) of 5-Bromo-2,4-dichloropyrimidine and 3.4 ml (24.0 mmol) of triethylamine in 10 ml of acetonitrile is mixed with 1.82 g (12.1 mmol) of trans-2-aminocyclohexanol hydrochloride. After 16 hours at room temperature the batch is filtrated and the filtrate is concentrated by evaporation. The remaining residue is purified by chromatography (hexane/ethyl acetate: 1:1). 1.61 g (5.3 mmol, corresponding to 53% of theory) of the product is obtained.

¹H-NMR (DMSO-D6): 8.21 (s, 1H), 7.11 (d, 1H), 4.68 (br, 1H), 3.78 (m, 1H), 3.53 (m, 1H), 1.87 (m, 2H), 1.62 (m, 2H), 1.23 (m, 4H).

12b) Production of End Product 95 mg (0,52 mmol) of intermediate 1.3 (N-(4-Aminophenyl)-S,S-dimethylsulfoximide, example 1) and 158 mg (0,52 mmol) of intermediate 12.1 (trans-2-(5-Bromo-2-chloro-pyrimidin-4-ylamino)-cyclohexanol) in 3.60 ml of acetonitrile and 0.24 ml of water are mixed with 0.13 ml of a 4N solution of HCl in dioxane. The batch is stirred for 3 hours at 60° C. An additional amount of 47 mg (0,26 mmol) of intermediate 1.3 (N-(4-Aminophenyl)-S,S-dimethylsulfoximide, example 1) is added and the batch is stirred for 10 hours at 60° C. The batch is concentrated by evaporation. The remaining residue is purified by chromatography (DCM/EtOH 85:15). 153 mg (0.34 mmol, corresponding to 65% of theory) of the product is obtained.

¹H-NMR (DMSO-D6): 8.82 (s, 1H), 7.91 (s, 1H), 7.48 (m, 2H), 6.75 (m, 2H), 6.18 (d, 1H), 4.68 (d, 1H), 3.70 (br, 1H), 3.47 (br, 1H), 3.10 (s, 6H), 1.95 (m, 2H), 1.63 (m, 2H), 1.20 (m, 4H).
MS: 454 (ES+).

EXAMPLE 13

N-[4-({5-Bromo-4-[(R)-(2,3,4,5-tetrahydrofuran-3-yl)amino]pyrimidin-2-yl}amino)phenyl]-S,S-dimethylsulfoximide

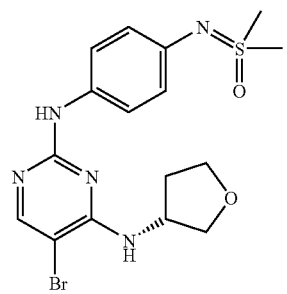

13a) Production of Intermediates

Intermediate 13.1

(5-Bromo-2-chloro-pyrimidin-4-yl)-(R)-tetrahydro-furan-3-yl-amine

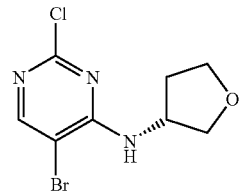

An ice-cooled solution of 1.82 g (8.0 mmol) of 5-Bromo-2,4-dichloropyrimidine and 2.8 ml (20.0 mmol) of triethylamine in 8 ml of acetonitrile is mixed with 2.04 g (7.9 mmol) of R(+)-3-Aminotetrahydrofuran toluene-4-sulfonate. After 16 hours at room temperature the batch is filtrated and the filtrate is concentrated by evaporation. The remaining residue is purified by chromatography (hexane/ethyl acetate: 4:1). 1.60 g (5.8 mmol, corresponding to 73% of theory) of the product is obtained.

¹H-NMR (DMSO-D6): 8.28 (s, 1H), 7.55 (d, 1H), 4.52 (m, 1H), 3.88 (m, 2H), 3.70 (m, 1H), 3.61 (m, 1H), 2.19 (m, 1H), 2.01 (m, 1H).

13b) Production of End Product 95 mg (0,52 mmol) of intermediate 1.3 (N-(4-Aminophenyl)-S,S-dimethylsulfoximide, example 1) and 143 mg (0,52 mmol) of intermediate 13.1 (5-Bromo-2-chloro-pyrimidin-4-yl)-(R)-tetrahydro-furan-3-yl-amine) in 3.60 ml of acetonitrile and 0.24 ml of water are mixed with 0.13 ml of a 4N solution of HCl in dioxane. The batch is stirred for 3 hours at 60° C. An additional amount of 47 mg (0,26 mmol) of intermediate 1.3 (N-(4-Aminophenyl)-S,S-dimethylsulfoximide, example 1) is added and the batch is stirred for 10 hours at 60° C. The batch is concentrated by evaporation. The remaining residue is purified by chromatography (DCM/EtOH 85:15). 67 mg (0.16 mmol, corresponding to 31% of theory) of the product is obtained.

$^1$H-NMR (DMSO-D6): 8.98 (s, 1H), 7.93 (s, 1H), 7.45 (m, 2H), 6.79 (m, 2H), 6.61 (d, 1H), 4.52 (m, 1H), 3.85 (m, 2H), 3.68 (m, 1H), 3.58 (m, 1H), 3.12 (s, 6H), 2.18 (m, 1H), 2.00 (m, 1H).

MS: 426 (EI).

EXAMPLE 14

(RS)—N-{4-[(5-Bromo-4-{[(R)-2-hydroxy-1,2-dimethylpropyl]amino}pyrimidin-2-yl) amino]phenyl}-S-ethyl-S-methylsulfoximide

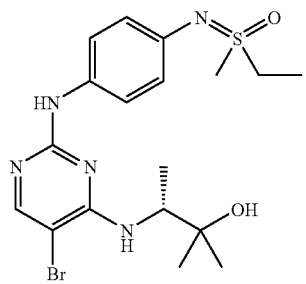

14a) Production of Intermediates

Intermediate 14.1

S-Ethyl-S-methyl-N-(4-nitrophenyl)sulfimide

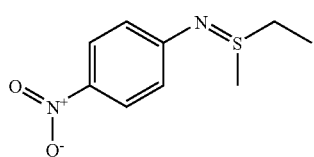

The compound is prepared according to the procedure for the preparation of intermediate 1.1.

$^1$H-NMR (DMSO): 7.70 (m, 2H), 6.32 (m, 2H), 3.15 (m, 1H), 2.89 (m, 1H), 2.70 (s, 3H), 1.18 (m, 3H).

Intermediate 14.2

(RS)—S-Ethyl-S-methyl-N-(4-nitrophenyl)sulfoximide

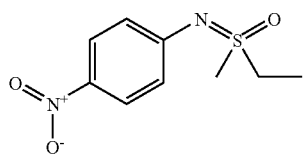

The compound is prepared according to the procedure for the preparation of intermediate 1.2.

$^1$H-NMR (DMSO): 8.05 (m, 2H), 7.08 (m, 2H), 3.40 (q, 2H), 3.24 (s, 3H), 1.27 (tr, 3H).

MS: 229 (ESI+).

Intermediate 14.3

(RS)—N-(4-Aminophenyl)-S-ethyl-S-methylsulfoximide

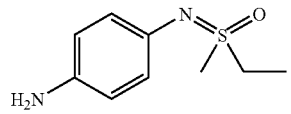

The compound is prepared according to the procedure for the preparation of intermediate 1.3.

$^1$H-NMR (DMSO): 6.61 (m, 2H), 6.38 (m, 2H), 4.56 (s, 2H), 3.15 (m, 2H), 2.91 (s, 3H), 1.20 (tr, 3H).

MS: 199 (ESI+).

14b) Production of End Product 164 mg (0,83 mmol) of intermediate 14.3 ((RS)—N-(4-Aminophenyl)-S-ethyl-S-methylsulfoximide) and 294 mg (1,00 mmol) of intermediate 1.5 ((R)-3-[(5-bromo-2-chloropyrimidin-4-yl)amino]-2-methyl-butan-2-ol) in 6.6 ml of isopropanole are mixed with 0.25 ml of a 4N solution of HCl in dioxane. The batch is stirred for 15 hours at 80° C. and then concentrated by evaporation. The remaining residue is purified by chromatography (DCM/EtOH 90:10). 70 mg (0.15 mmol, corresponding to 18% of theory) of the product is obtained.

$^1$H-NMR (DMSO): 10.49 (s, 1H), 8.21 (s, 1H), 7.28 (m, 3H), 6.91 (m, 2H), 4.01 (m, 1H), 3.33 (q, 2H), 3.08 (s, 3H), 1.21 (tr, 3H), 1.08 (m, 9H).

MS: 456 (ES+).

EXAMPLE 15

N-{4-[(5-Ethyl-4-{[(R)-1-(hydroxymethyl)-2-methylpropyl]amino}pyrimidin-2-yl) amino]phenyl}-S,S-dimethylsulfoximide

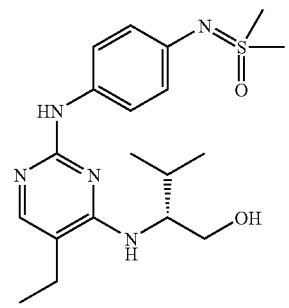

15a) Production of Intermediates

Intermediate 15.1

(R)-2-(2-Chloro-5-ethyl-pyrimidin-4-ylamino)-3-methyl-butan-1-ol

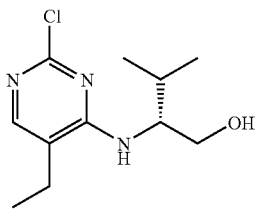

A solution of 882 mg (5.0 mmol) of 2,4-Dichloro-5-ethyl-pyrimidine and 0.75 ml (5.5 mmol) triethylamine in 5 ml of acetonitrile is mixed with 672 mg (6.5 mmol) of (R)-2-Amino-3-methyl-butan-1-ol. The batch is stirred at room temperature for 16 hours and is finally concentrated by evaporation. The remaining residue is purified by chromatography (DCM/EtOH 90:10). 742 mg of the product is obtained that still contains considerable amounts of (R)-2-Amino-3-methyl-butan-1-ol. The material is used without further purifications.

15b) Production of End Product 38 mg (0,21 mmol) of intermediate 1.3 (N-(4-Aminophenyl)-S,S-dimethylsulfoximide, example 1) and 101 mg of intermediate 15.1 ((R)-2-(2-Chloro-5-ethyl-pyrimidin-4-ylamino)-3-methyl-butan-1-ol) in 1.00 ml of acetonitrile are mixed with 0.06 ml of a 4N solution of HCl in dioxane. The batch is stirred for 18 hours at 80° C. The batch is concentrated by evaporation. The remaining residue is purified by chromatography (DCM/EtOH 80:20). 5 mg (0.01 mmol, corresponding to 6% of theory) of the product is obtained.

$^1$H-NMR (DMSO): 9.15 (br, 1H), 7.58 (s, 1H), 7.40 (m, 2H), 6.79 (m, 2H), 6.63 (d, 1H), 4.60 (br, 1H), 4.04 (m, 1H), 3.55 (m, 2H), 3.12 (s, 6H), 2.36 (m, 2H), 1.95 (m, 1H), 1.07 (tr, 3H), 0.88 (m, 6H).

MS: 392 (ES+)

EXAMPLE 16

N-{4-[(5-Bromo-4-{[(R)-2-hydroxy-1,2-dimethyl propyl]amino}pyrimidin-2-yl)amino]phenyl}-S,S-(butane-1,4-diyl)sulfoximide

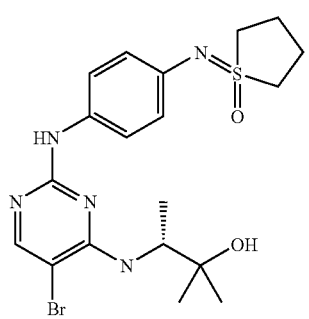

16a) Production of Intermediates

Intermediate 16.1

S,S-(Butane-1,4-diyl)-N-(4-nitrophenyl)sulfimide

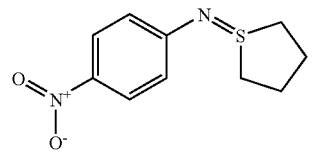

The compound is prepared according to the procedure for the preparation of intermediate 1.1.

$^1$H-NMR (DMSO): 7.85 (m, 2H), 6.61 (m, 2H), 3.41 (m, 2H), 2.80 (m, 2H), 2.25 (m, 2H), 2.02 (m, 2H).

MS: 225 (ESI+)

Intermediate 16.2

S,S-(Butane-1,4-diyl)-N-(4-nitrophenyl)sulfoximide

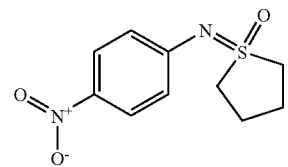

The compound is prepared according to the procedure for the preparation of intermediate 1.2.

$^1$H-NMR (DMSO): 8.04 (m, 2H), 7.00 (m, 2H), 3.41 (m, 4H), 2.22 (m, 2H), 2.08 (m, 2H).

MS: 241 (ESI+)

Intermediate 16.3

N-(4-Aminophenyl)-S,S-(butane-1,4-diyl)sulfoximide

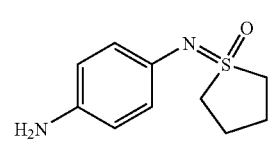

The compound is prepared according to the procedure for the preparation of intermediate 1.3.

$^1$H-NMR (DMSO): 6.60 (m, 2H), 6.40 (m, 2H), 4.58 (s, 2H), 3.19 (m, 2H), 3.02 (m, 2H), 2.11 (m, 2H), 2.01 (m, 2H).

MS: 211 (ES+)

16b) Production of End Product 40 mg (0,19 mmol) of intermediate 16.3 (N-(4-Aminophenyl)-S,S-(butane-1,4-diyl)sulfoximide) and 70 mg (0.24 mmol) of intermediate 1.5 ((R)-3-[(5-bromo-2-chloropyrimidin-4-yl)amino]-2-methyl-butan-2-ol) in 1.5 ml of isopropanole are mixed with 0.05 ml of a 4N solution of HCl in dioxane. The batch is stirred for 15 hours at 60° C. and then concentrated by evaporation. The remaining residue is purified by chromatography.

Assay 1

CDK1/CycB Kinase Assay

Recombinant CDK1- and CycB-GST-fusion proteins, purified from baculovirus-infected insect cells (Sf9), were purchased from ProQinase GmbH, Freiburg. Histone IIIS, used as a kinase substrate, is available commercially from the Sigma Company.

CDK1/CycB (200 ng/measuring point) was incubated for 15 minutes at 22° C. in the presence of various concentrations of test substances (0 µm, as well as within the range of 0.01-100 µm) in assay buffer [50 mmol of tris/HCl, pH 8.0, 10 mmol of $MgCl_2$, 0.1 mmol of Na ortho-vanadate, 1.0 mmol of dithiothreitol, 0.5 µm of adenosine triphosphate (ATP), 10 µg/measuring point of histone IIIS, 0.2 µCi/measuring point of $^{33}$P-gamma ATP, 0.05% NP40, 12.5% dimethyl sulfoxide]. The reaction was stopped by adding EDTA solution (250 mmol, pH 8.0, 14 µl/measuring point).

From each reaction batch, 10 µl was applied to P30 filter strips (Wallac Company), and non-incorporated 33P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated 33P (substrate phosphorylation) was determined by scintillation measurement in a gamma-radiation measuring device (Wallac).

Assay 2

CDK2/CycE Kinase Assay

Recombinant CDK2- and CycE-GST-fusion proteins, purified from baculovirus-infected insect cells (Sf9), were purchased by ProQinase GmbH, Freiburg. Histone IIIs, which was used as a kinase substrate, was purchased by the Sigma Company.

CDK2/CycE (50 ng/measuring point) was incubated for 15 minutes at 22° C. in the presence of various concentrations of test substances (0 µm, as well as within the range of 0.01-100 µm) in assay buffer [50 mmol of tris/HCl, pH 8.0, 10 mmol of $MgCl_2$, 0.1 mmol of Na ortho-vanadate, 1.0 mmol of dithiothreitol, 0.5 µm of adenosine triphosphate (ATP), 10 µg/measuring point of histone IIIS, 0.2 µCi/measuring point of $^{33}$P-gamma ATP, 0.05% NP40, 12.5% dimethyl sulfoxide]. The reaction was stopped by adding EDTA solution (250 mmol, pH 8.0, 14 µl/measuring point).

From each reaction batch, 10 µl was applied to P30 filter strips (Wallac Company), and non-incorporated $^{33}$P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated $^{33}$P (substrate phosphorylation) was determined by scintillation measurement in a gamma-radiation measuring device (Wallac).

Assay 3

VEGF Receptor-2 Kinase Assay

Recombinant VEGF receptor tyrosine kinase-2 was purified as a GST fusion protein from baculovirus-infected insect cells (Sf9). Poly-(Glu4Tyr), which was used as a kinase substrate, was purchased by the Sigma Company. VEGF receptor tyrosine kinase (90 ng/measuring point) was incubated for 10 minutes at 22° C. in the presence of various concentrations of test substances (0 µm, as well as within the range of 0.001-30 µm) in 30 µl of assay buffer [40 mmol of Tris/HCl, pH 5.5, 10 mmol of $MgCl_2$, 1 mmol of $MnCl_2$, 3 µmol of Na orthovanadate, 1.0 mmol of dithiothreitol, 8 µmol of adenosine trisphosphate (ATP), 27 µg/measuring point of poly-(Glu4Tyr), 0.2 µCi/measuring point of 33P-gamma ATP, 1% dimethyl sulfoxide]. The reaction was stopped by adding EDTA solution (250 mmol, pH 7.0, 10 µl/measuring point).

From each reaction batch, 10 µl was applied to P30 filter strips (Wallac Company), and non-incorporated 33P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated 33P (substrate phosphorylation) was determined by scintillation measurement in a gamma-radiation measuring device (Wallac). The IC50 values are determined from the inhibitor concentration, which is necessary to inhibit the phosphate incorporation to 50% of the uninhibited incorporation after removal of the blank reading (EDTA-stopped reaction).

Assay 4

Proliferation Assay

Cultivated human tumor cells (MCF7, hormone-independent human breast cancer cells, related to ATCC HTB22; NCI-H460, human non-small-cell lung cancer cells, ATCC HTB-177; DU 145, hormone-independent human prostate cancer cells, ATCC HTB-81; MaTu-MDR, hormone-independent, multiple pharmaceutical agent-resistant human breast cancer cells, EPO-GmbH, Berlin) were flattened out at a density of about 5000 cells/measuring point, depending on the growth rate of the respective cells, in a 96-well multititer plate in 200 µl of the corresponding growth medium. After 24 hours, the cells of one plate (zero-point plate) were colored with crystal violet (see below), while the medium of the other plates was replaced by fresh culture medium (200 µl), to which the test substances were added in various concentrations (0 µm, as well as in the range of 0.01-30 µm; the final concentration of the solvent dimethyl sulfoxide was 0.5%). The cells were incubated for 4 days in the presence of test substances. The cell proliferation was determined by coloring the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were colored by adding 100 µl/measuring point of a 0.1% crystal violet solution (the pH was set at 3 by adding acetic acid). After three washing cycles of the colored cells with water, the plates were dried at room temperature. The dye was dissolved by adding 100 µl/measuring point of a 10% acetic acid solution. The extinction was determined by photometry at a wavelength of 595 nm. The change of cell growth, in percent, was calculated by normalization of the measured values to the extinction values of the zero-point plate (=0%) and the extinction of the untreated (0 µm) cells (=100%).

Assay 5

Carboanhydrase Assay

The principle of the assay is based on the hydrolysis of 4-nitrophenyl acetate by carboanhydrases (Pocker & Stone, *Biochemistry*, 1967, 6, 668), with subsequent photometric determination of the dye 4-nitrophenolate that is produced at 400 nm by means of a 96-channel spectral photometer.

2 µl of the test compounds, dissolved in DMSO (100× the final concentration), in a concentration range of 0.03-10 µm (final), was pipetted as 4× determinations into the holes of a 96-hole microtiter plate. Holes that contained the solvent without test compounds were used as reference values (1. Holes without carboanhydrase for correction of the non-enzymatic hydrolysis of the substrate, and 2. Holes with carboanhydrase for determining the activity of the non-inhibited enzyme).

188 μl of assay buffer (10 mmol of Tris/HCl, pH 7.4, 80 mmol of NaCl), with or without 3 units/hole on carboanhydrase I or II, was pipetted into the holes of the microtiter plate. The enzymatic reaction was started by the addition of 10 μl of the substrate solution (1 mmol of 4-nitrophenyl acetate (Fluka #4602), dissolved in anhydrous acetonitrile (final substrate concentration: 50 μm). The plate was incubated at room temperature for 15 minutes. The extinctions were measured by photometry at a wavelength of 400 nm. The enzyme inhibition was calculated after the measured values were normalized to the extinction of the reactions in the holes without enzyme (=100% inhibition) and to the extinction of reactions in the holes with non-inhibited enzyme (=0% inhibition).

The results from the examples and the comparison data are indicated in Tables 1 to 3 below. To demonstrate the superiority of the compounds according to the invention compared to the known compounds, the compounds according to the invention were compared to known reference compounds and a structurally similar known compound of Example 10 from WO 00/096888 in the enzyme test. The result is indicated in Tables 1 and 2 below. In Table 3, the improved data on the compounds according to the invention are shown in comparison to the compound of Example 10 from WO 00/12486 and acetazolamide.

TABLE 1

| | Proliferation IC$_{50}$ [μM] | | | |
|---|---|---|---|---|
| Example No. | MCF7 | H460 | DU145 | MaTu-ADR |
| 1 | 0.4 | 0.5 | 0.6 | 0.8 |
| 2 | 0.6 | 0.8 | 1 | 0.9 |
| 3 | 0.3 | 0.7 | 1 | 0.5 |
| 4 | 2.2 | | | |
| 5 | 0.7 | | | |
| 6 | 0.5 | 0.4 | 0.3 | 0.3 |
| Expl. 10/WO 02/096888 | 0.4 | 0.6 | 0.7 | 0.8 |

TABLE 2

| Example No. | CDK2/CycE IC$_{50}$ [nM] | CDK1/CycB IC$_{50}$ [nM] | VEGF-R2 IC$_{50}$ [nM] |
|---|---|---|---|
| 1 | 27 | 130 | 74 |
| 2 | 11 | 32 | 27 |
| 3 | 12 | 28 | 44 |
| 4 | 200 | 1000 | 88 |
| 5 | 340 | 490 | 180 |
| 6 | 1000 | 1000 | 73 |
| 7 | 1000 | 1000 | 200 |
| 9 | 260 | 670 | 140 |
| 10 | 220 | 400 | 160 |
| 11 | 680 | 1000 | 54 |
| 12 | 460 | 1000 | 280 |
| 13 | 1000 | 1000 | 42 |
| Expl. 10/WO 02/096888 | <10 | 90 | 200 |

TABLE 3

| Example No. | Inhibition of Human Carboanhydrase-2 IC$_{50}$ [nM] |
|---|---|
| 1 | >10000 |
| 2 | >10000 |
| 3 | >10000 |

TABLE 3-continued

| Example No. | Inhibition of Human Carboanhydrase-2 IC$_{50}$ [nM] |
|---|---|
| Acetazolamide | 51 |
| Expl. 10/WO 02/096888 | 190 |

Tables 1 and 2 show that the compounds according to the present invention inhibit cyclin-dependent kinases and VEGF receptor tyrosine kinases in the nanomolar range and thus may inhibit the proliferation of tumor cells and/or the tumor angiogenesis.

Table 3 shows that substances according to the invention, in contrast to compounds from the prior art, such as, e.g., acetazolamide or Example 10 from WO02/096888, which represents the closest prior art, do not have any measurable carboanhydrase inhibiton and thus no longer exhibit a possible side effect that could be attributed to the carboanhydrase inhibition.

In this respect, the above-mentioned tables confirm that the substances according to the invention are superior in comparison to the prior art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding European application No. 05090073.7, filed Mar. 23, 2005, and U.S. Provisional Application Ser. No. 60/665,862, filed Mar. 29, 2005 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I)

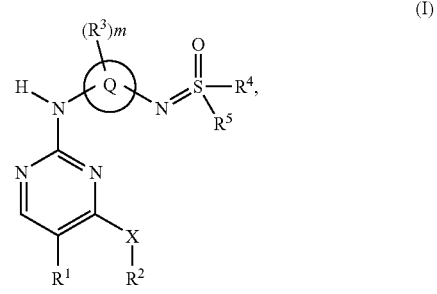

in which

Q stands for phenyl, $R^1$ stands for halogen, —$CF_3$, $C_1$-$C_4$-Alkyl or Nitro, $R^2$ stands for $C_1$-$C_{10}$-alkyl, $C_2$-$C_{10}$-alkenyl, $C_2$-$C_{10}$-alkinyl, $C_3$-$C_{10}$-cycloalkyl, heterocyclyl with 3 to 7 ring atoms, $C_n$-aryl or heteroaryl with 5 to 10 ring atoms, each of which is optionally substituted in one or more places, in the same way or differently, with
(i) hydroxy, halogen, —$NR^7R^8$ or with the group —$COR^6$, and/or
(ii) $C_1$-$C_4$-alkyl, $C_2$-$C_4$-alkenyl, $C_1$-$C_4$-alkoxy, $C_2$-$C_4$-alkinyl, which is optionally substituted in one or more places, in the same way or differently, with hydroxy, halogen, —$NR^7R^8$ or with the group —$COR^6$, X stands for —O—, —S— or for the group —NH— or —$NR^{11}$—, wherein $R^{11}$ is a $C_1$-$C_3$-Alkyl, or in case X stands for the group —$NR^{11}$—

$R^2$, $R^{11}$ and X form together a heterocyclyl ring with 3 to 7 ring atoms, which optionally contains one or more additional heteroatoms and optionally is substituted in one or more places in the same way or differently, with hydroxy, $C_1$-$C_3$-alkyl, $C_1$-$C_3$-alkoxy, —$NR^7R^8$ or halogen, $R^3$ stands for hydroxy, halogen, —$CF_3$, —$OCF_3$ or for the group —$NR^7R^8$, or for $C_1$-$C_6$-alkyl, $C_3$-$C_6$-cycloalkyl or $C_1$-$C_6$-alkoxy, each of which is optionally substituted in one or more places, in the same way or differently, with halogen, hydroxy or the group —$NR^7R^8$, m stands for 0-4, $R^4$ and $R^5$ in each case independently of one another, stand for $C_1$-$C_6$-alkyl, $C_1$-$C_6$-alkenyl or $C_3$-$C_6$-cycloalkyl, each of which is optionally substituted in one or more places, in the same way or differently, with hydroxy, halogen, $C_1$-$C_3$-alkoxy, $C_1$-$C_3$-alkylthio, cyano, $C_3$-$C_6$-cycloalkyl, $C_1$-$C_6$-hydroxyalkyl, $C_2$-$C_6$-alkenyl, $C_2$-$C_6$-alkinyl or with the group —$CF_3$, —$OCF_3$ or —$NR^7R^8$, or $R^4$ and $R^5$ together form a ring of the group

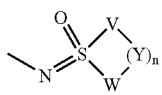

V, W and Y stand for —$CH_2$—, which are optionally and independently substituted in one or more places, in the same way or differently, with halogen, hydroxy, $C_1$-$C_6$-alkyl, $C_1$-$C_6$-alkoxy or —$NR^7R^8$, n stands for 0-4, $R^6$ stands for hydrogen or $C_1$-$C_6$-alkyl, $C_1$-$C_6$-alkoxy or $C_3$-$C_6$-cycloalkyl, each of which is optionally substituted in one or more places, in the same way or differently, with $C_1$-$C_6$-alkyl, $R^7$ and $R^8$ in each case independently of one another, stand for hydrogen, $C_1$-$C_6$-alkyl, $C_1$-$C_6$-alkoxy, hydroxy-$C_1$-$C_6$-alkyl, dihydroxy-$C_1$-$C_6$-alkyl, phenyl, heteroaryl or for the group —$(CH_2)_p NR^9R^{10}$, or $R^7$ and $R^8$ form together with the nitrogen atom a heterocycyl ring with 3 to 7 ring atoms, which optionally contain one or more nitrogen, oxygen and/or sulfur atoms and/or can be interrupted by one or more —C(O)— groups in the ring, $R^9$ and $R^{10}$ in each case independently of one another, stand for hydrogen, $C_1$-$C_6$-alkyl, hydroxy-$C_1$-$C_6$-alkyl, dihydroxy-$C_1$-$C_6$-alkyl and p stands for 0-4, or a diastereomer, enantiomer or salt thereof.

2. A compound according to claim 1, wherein $R^1$ stands for halogen, —$CF_3$, $C_1$-$C_2$-Alkyl or Nitro.

3. A compound according to claim 1, wherein $R^1$ stands for bromine.

4. A compound according to claim 1, wherein $R^2$ stands for $C_1$-$C_{10}$-alkyl, $C_2$-$C_{10}$-alkinyl, $C_3$-$C_{10}$-cycloalkyl, heterocyclyl with 3 to 7 ring atoms, $C_n$-aryl or a monocyclic heteroaryl, each of which is optionally substituted in one or more places, in the same way or differently, with hydroxy and/or $C_1$-$C_4$-alkyl, which is optionally substituted in one or more places, in the same way or differently wth hydroxyl.

5. A Compound according to claim 1, wherein $R^2$ stands for $C_2$-$C_6$-alkyl, $C_2$-$C_8$-alkinyl, $C_4$-$C_7$-cycloalkyl, heterocyclyl with 5 to 7 ring atoms, phenyl or a monocyclic heteroaryl with 6 ring atoms, each of which is optionally substituted in one or more places, in the same way or differently, with hydroxy and/or $C_1$-$C_4$-alkyl, which is optionally substituted in one or more places, in the same way or differently with hydroxyl.

6. A compound according to claim 1, wherein $R^2$ stands for $C_3$-$C_5$-alkyl, $C_3$-$C_5$-alkinyl, $C_5$-$C_6$-cycloalkyl, heterocyclyl with 6 ring atoms, phenyl or monocyclic heteroaryl with 6 ring atoms and only one heteroatom, each of which is optionally substituted in one or more places, in the same way or differently, with hydroxy and/or $C_1$-$C_4$-alkyl, which is optionally substituted in one or more places, in the same way or differently with hydroxyl.

7. A compound according to claim 1, wherein X stands for —O—, —S— or for the group —NH—.

8. A compound according to claim 1, wherein X stands for —NH—.

9. A compound according to claim 1, wherein m stands for 0 or 1.

10. A compound according to claim 1, wherein $R^4$ and $R^5$ independently stand for $C_1$-$C_6$-alkyl which is optionally substituted in one or more places, in the same way or differently, with hydroxy, halogen, $C_1$-$C_3$-alkoxy, $C_1$-$C_6$-hydroxyalkyl or —$NR^7R^8$ or $R^4$ and $R^5$ together form a ring of the group

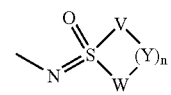

V, W and Y stand for —$CH_2$—, which are optionally and independently substituted in one or more places, in the same way or differently, with halogen, hydroxy, $C_1$-$C_6$-alkyl, $C_1$-$C_6$-alkoxy or —$NR^7R^8$, and n stands for 1-3.

11. A compound according to claim 1, wherein $R^4$ and $R^5$ independently stand for $C_1$-$C_6$-alkyl which is optionally substituted in one or more places, in the same way or differently, with hydroxyl or —$NR^7R^8$, or $R^4$ and $R^5$ together form a ring of the group

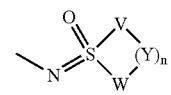

V, W and Y stand for —$CH_2$—, which are optionally and independently substituted in one or more places in the same way or differently with hydroxyl or —$NR^7R^8$, and n stands for 1-3.

12. A compound according to claim 1, wherein in case of a $NR^7R^8$-substituent $R^7$ and $R^8$ stand in each case independently of one another for hydrogen, $C_1$-$C_6$-alkyl, hydroxy-$C_1$-$C_6$-alkyl, dihydroxy-$C_1$-$C_6$-alkyl or for the group —$(CH_2)_pNR^9R^{10}$ or $R^7$ and $R^8$ form together with the nitrogen atom a heterocycyl ring with 5 or 6 ring atoms which is optionally interrupted by one —C(O)— group in the ring and/or can be substituted by hydroxy, $C_1$-$C_6$-alkyl, hydroxy-$C_1$-$C_6$-alkyl or dihydroxy-$C_1$-$C_6$-alkyl.

13. A compound according to claim 1, wherein $R^1$ stands for halogen, —$CF_3$, $C_1$-$C_2$-Alkyl or Nitro, $R^2$ stands for $C_1$-$C_{10}$-alkyl, $C_2$-$C_{10}$-alkinyl, $C_3$-$C_{10}$-cycloalkyl, heterocyclyl with 3 to 7 ring atoms, $C_n$-aryl or a monocyclic heteroaryl each of which is optionally substituted in one or more places, in the same way or differently, with hydroxy and/or $C_1$-$C_4$-alkyl, which is optionally substituted in one or more places, in the same way or differently with hydroxyl, X stands for —O—, —S— or for the group —NH—, m stands for 0, $R^4$ and $R^5$ independently stand for $C_1$-$C_6$-alkyl which is optionally substituted in one or more places, in the same way or differently, with hydroxyl or —$NR^7R^8$, or $R^4$ and $R^5$ together form a ring of the group

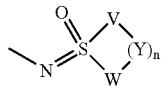

V, W and Y stand for —$CH_2$—, which are optionally and independently substituted in one or more places in the same way or differently with hydroxyl or —$NR^7R^8$, n stands for 1-3.

14. A compound according to claim 13, wherein $R^1$ stands for bromine.

15. A compound according to claim 14, wherein $R^2$ stands for $C_2$-$C_6$-alkyl, $C_2$-$C_8$-alkinyl, $C_4$-$C_7$-cycloalkyl, heterocyclyl with 5 to 7 ring atoms, phenyl or a monocyclic heteroaryl with 6 ring atoms each of which is optionally substituted in one or more places, in the same way or differently, with hydroxy and/or $C_1$-$C_4$-alkyl, which is optionally substituted in one or more places, in the same way or differently with hydroxyl.

16. A compound according to claim 14, wherein $R^2$ stands for $C_3$-$C_5$-alkyl, $C_3$-$C_5$-alkinyl, $C_5$-$C_6$-cycloalkyl, heterocyclyl with 6 ring atoms, phenyl or monocyclic heteroaryl with 6 ring atoms and only one heteroatom each of which is optionally substituted in one or more places, in the same way or differently, with hydroxy and/or $C_1$-$C_4$-alkyl, which is optionally substituted in one or more places, in the same way or differently with hydroxyl.

17. A compound according to claim 13, wherein X stands for —NH—.

18. A compound according to claim 13, wherein $R^4$ and $R^5$ independently stand for $C_1$-$C_6$-alkyl or $R^4$ and $R^5$ together form a ring of the group

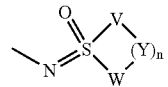

V, W and Y stand for —$CH_2$—, and n stands for 2.

19. A pharmaceutical composition comprising a pharmaceutically acceptable carrier and a compound according to claim 1.

20. A process for preparing a compound of Formula (I) according to claim 1, comprising

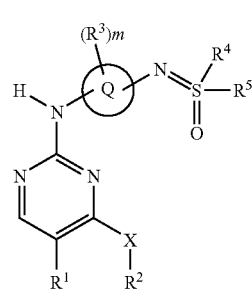

coupling a compound of formula (II)

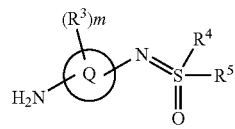

with a compound of formula (III)

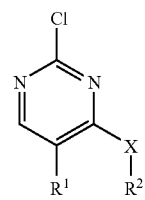

under acidic conditions, wherein Q, X, R1, R2, R3, R4, and R5 have the meanings indicated for formula I.

21. A pharmaceutical composition comprising a pharmaceutically acceptable carrier and a compound according to claim 2.

22. A pharmaceutical composition according to claim 19, which is suitable for enteral, parenteral or oral administration.

23. A pharmaceutical composition according to claim 21, which is suitable for enteral, parenteral and oral administration.

24. A method for treating hormone-independent human breast cancer comprising administering to a patient in need thereof an effective amount of a pharmaceutical composition according to claim 19.

25. A method for treating human non-small-cell lung cancer comprising administering to a patient in need thereof an effective amount of a pharmaceutical composition according to claim 19.

26. A method for treating hormone-independent human prostate cancer comprising administering to a patient in need thereof an effective amount of a pharmaceutical composition according to claim 19.

27. A method for treating hormone-independent, multiple pharmaceutical agent-resistant human breast cancer comprising administering to a patient in need thereof an effective amount of a pharmaceutical composition according to claim 19.

* * * * *